United States Patent [19]

Harkki et al.

[11] Patent Number: 5,631,150
[45] Date of Patent: May 20, 1997

[54] MANUFACTURING OF XYLITOL USING RECOMBINANT MICROBIAL HOSTS

[75] Inventors: Anu M. Harkki, Espoo; Andrey N. Myasnikov, Kantvik; Juha H. A. Apajalahti, Helsinki; Ossi A. Pastinen, Kantvik, all of Finland

[73] Assignee: Xyrofin Oy, Kotka, Finland

[21] Appl. No.: 368,395

[22] Filed: Jan. 3, 1995

Related U.S. Application Data

[63] Continuation of Ser. No. 110,672, Aug. 24, 1993, abandoned, which is a continuation-in-part of Ser. No. 973,325, Nov. 5, 1992, abandoned.

[51] Int. Cl.$^6$ .............................. C12P 19/02; C12N 1/15; C12N 1/19
[52] U.S. Cl. .................. 435/105; 435/254.11; 435/254.2
[58] Field of Search .......................... 435/72, 105, 172.3, 435/183, 193, 254, 254.11, 254.2, 254.21–254.23; 536/23.1, 23.2, 23.7

[56] References Cited

U.S. PATENT DOCUMENTS

| | | | |
|---|---|---|---|
| 3,586,537 | 6/1971 | Steiner et al. | 127/37 |
| 3,619,369 | 11/1971 | Onishi et al. | 435/158 |
| 3,784,408 | 1/1974 | Jaffe et al. | 127/37 |
| 4,008,285 | 2/1977 | Melaja et al. | 568/863 |
| 4,066,711 | 1/1978 | Melaja et al. | 568/827 |
| 4,075,406 | 2/1978 | Melaja et al. | 536/127 |
| 5,081,026 | 1/1992 | Heikkilä et al. | 435/158 |

FOREIGN PATENT DOCUMENTS

| | | |
|---|---|---|
| 0450430A2 | 10/1991 | European Pat. Off. |
| 2641545 | 7/1990 | France. |
| 4009676A1 | 10/1991 | Germany. |
| WO88/05467 | 7/1988 | WIPO. |
| WO90/08193 | 1/1990 | WIPO. |
| WO91/10740 | 7/1991 | WIPO. |
| WO91/15588 | 10/1991 | WIPO. |

OTHER PUBLICATIONS

Bailey, J.E., "Toward a Science of Metabolic Engineering," *Science* 252:1668–1675 (1991).

Maniatis, T. et al., "Molecular Cloning: A Laboratory Manual," (Cold Spring Harbor Laboratory Press, CSH), pp. 269–294.

Hagedorn, J. et al., "Isolation and characterization of xyl mutants in a xylose–utilizing yeast, *Pichia stipitis*," *Chem. Abstracts* 111:No. 228807q (1989).

Hagedorn, J. et al., "Isolation and characterization of xyl mutants in a xylose–utilizing yeast, *Pichia stipitis*," *Curr. Genet.* 16:27–33 (1989).

Takuma, S. et al., "Isolation of Xylose Reductase Gene of *Pichia stipitis* and its Expression In *Saccharomyces cerevisiae*", *Appl. Biochem./Biotech.* 28/29:327–340 (1991).

Barbosa, M.F.S. et al., "Screening of yeasts for production of xylitol from D–xylose and some factors which affect xylitol yield in *Candida guilliermondii*," *J. Industrial Microbiol.* 3:241–251 (1988).

Hallborn, J. et al., "Xylitol Production by Recombinant *Saccharomyces cerevisiae*," *Biotechnology* 9:1090–1095 (1991).

Lewis D.H. and Smith, D.C., "Sugar Alcohols (Polyols) in Fungi and Green Plants," *New Phytol.* 66:143–184 (1967).

Onishi, H. et al., "Microbial Production of Xylitol from Glucose," *Appl. Microbiol.* 18:1031–1035 (1969).

Ingram, J.M. et al., "Enzymatic Basis for D–Arabitol Production by *Saccharomyces rouxii*," *J. Bacteriol.* 89:1186–1194 (1965).

Haahtela et al., "Nitrogenase Activity (Acetylene Reduction) of Root–Associated, Cold–Climate *azospirillum, enterobacter, klebsiella,* and *pseudomonas* Species During Growth on Various Carbon Sources and at Various partial Pressures of Oxygen," *Appl. Env. Microbiol.* 45:563–570 (1983).

Kötter, P. et al., "Isolation and characterization of the *Pichia stipitis* Xylitol dehydrogenase gene, XYL2, and construction of a xylose–utilizing *Saccharomyces cerevisiae* transformant," *Curr. Genet.* 18:493–500 (1990).

Ushio, K. et al., "Construction of a Host–Vector System in the Osmophilic Haploid Yeast *Zygosaccharomyces rouxii*," *J. Ferment. Technol.* 66:481–488 (1988).

Hattori, K. and Suzuki T., "Microbial Production of D–Arabitol by *n*–Alkane–grown *Candida tropicalis*," *Agric. Biol. Chem.* 38:1875–1881 (1974).

Haas, L. et al., "Development of an Integrative DNA Transformation System for the Yeast *Candida tropicalis*," *J. Bacteriol.* 172:4571–4577 (1990).

Nogae, I. and Johnston, M., "Isolation and characterization of the ZWF1 gene of *Saccharomyces cerevisiae*, encoding glucose–6–phosphate dehydrogenase," *Gene* 96:161–169 (1990).

Thomas, D. et al., "Identification of the structural gene for a glucose–6–phosphate dehydrogenase in yeast. Inactivation leads to a nutritional requirement for organic sulfur," *EMBO J.* 10:547–553 (1991).

Nasoff, M.S. et al., "DNA sequence of the *Escherichia coli gnd* gene, for 6–phosphogluconate dehydrogenase," *Gene* 27:253–264 (1984).

Loviny, T. et al., "Ribitol dehydrogenase of *Klebsiella aerogenes*; Sequence of the structural gene," *Biochem. J.* 230:579–585 (1985).

Williamson, W.T. et al., "D–Ribulose 5–Phosphate 3–Epimerase," *Meth. Enzymol.* 9:605–608 (1966).

Ho, N.W.Y. et al., "Cloning of yeast xylulokinase gene by complementation of *E. coli* and yeast mutations," *Enzyme Microbiol. Technol.* 11:417–421 (1989).

Stevis, P.E. et al., "Cloning of the *Pachysolen tannophilus* Xylulokinase Gene by Complementation in *Escherichia coli*," *Applied and Environ. Microbiol.* 53:2975–2977 (1987).

(List continued on next page.)

Primary Examiner—George C. Elliott
Attorney, Agent, or Firm—Sterne, Kessler, Goldstein & Fox, P.L.L.C.

[57] ABSTRACT

Novel methods for the synthesis of xylitol are described.

29 Claims, 13 Drawing Sheets

OTHER PUBLICATIONS

Stevis, P.E. et al., "Construction of Yeast Xylulokinase Mutant by Recombinant DNA Techniques," *Appl. Biochem. Biotechnol.* 20:327–334 (1989).

*The Yeasts, A Taxonomic Study*, Kreger-van Rij, M.J.W. (ed.), Elsevier Science publishers B.V., Amsterdam, 1984, pp. 462–465.

*Biological Chemistry*, H.R. Mahler & E.H. Cordes, Harper & Row, publishers, New York, 1966, pp. 448–454.

Ammerer, G., "Expression of Genes in Yeast Using the ADCI Promoter," *Meth. Enzymol.* 101C:192–201 (1983).

Aho, S., "Structural and functional analysis of *Trichoderma reesei* endoglucanase I expressed in yeast *Saccharomyces cerevisiae*," *FEBS Lett.* 291:45–49 (1991).

Toh-E.A. et al., "2-μm DNA-Like Plasmids in the Osmophilic Haploid Yeast *Saccharomyces rouxii*," *J. Bacteriol.* 151:1380–1390 (1982).

Toh-E.A. et al., "Plasmids Resembling 2-μm DNA in the Osmotolerant Yeasts *Saccharomyces bailii* and *Saccharomyces bisporus*," *J. Gen. Microbiol.* 130:2527–2534 (1984).

Jearnipipatkul, A. et al., "Factors encoded by and affecting the holding stability of yeast plasmid pSR1," *Mol. Gen. Genet.* 206:84–94 (1987).

Rothstein, R.J., "One-Step Gene Disruption in Yeast," *Meth. Enzymol.* 101C:202–211 (1983).

Ito, H. et al., "Transformation of Intact Yeast Cells Treated with Alkali Cations," *J. Bacteriol.* 153:163–168 (1983).

Lopes, T.S. et al., "High-copy-number integration into the ribosomal DNA of *Saccharomyces cerevisiae*: a new vector for high-level expression," *Gene* 79:199–206 (1989).

Gatignol, A. et al., "Cloning of *Saccharomyces cerevisiae* promoters using a probe vector based on phleomycin resistance," *Gene* 91:35–41 (1990).

Beggs, J.D., "Transformation of yeast by a replicating hybrid plasmid," *Nature* 275:104–109 (1978).

Gong, C.-S., et al., "Conversion of Pentoses by Yeasts," *Biotechnol. Bioeng.* 25:85–102 (1983).

James. A.P. et al., "Genetic and Biochemical Characterization of Mutations Affecting the Ability of the Yeast *Pachysolen tannophilus* To Metabolize D-Xylose," *Appl. and Environ. Microbiol.* 55(11):2871–2876 (1989).

Lee, H. et al., "Effect of biotin limitation on the conversion of xylose to ethanol and xylitol by *Pachysolen tannophilus* and *Candida guilliermondii*," *Enzyme Microb. Technol.* 10:81–84 (1988).

Holligan, P.M. et al., "Carbohydrate Metabolism In The Fungus *Dendryphiella salina*. I Changes In The Levels Of Soluble Carbohydrates During Growth," *New Phytol.* 71:569–582 (1972).

Jearnpipatkul, A. et al., "Factors encoded by and affecting the holding stability of yeast plasmid pSR1," *Mol. Gen. Genet.* 206:88–94 (1987).

Sarthy, A.V. et al., "Expression of the *Escherichia coli* Xylose Isomerase Gene in *Saccharomyces cerevisiae*," *Appl. Environ. Microbiol.* 53(9):1996–2000 (Sep. 1987).

Speth, J.L. et al., "Enzyme Activities Associated with Arabitol and Mannitol Biosynthesis and Catabolism in *Schizophyllum commune*," *Arch. Microbiol.* 107:81–86 (1976).

Sugihara, K. et al., "Ribosomal DNA Plasmid Isolated from *Zygosaccharomyces bailii* and Its Use for Constructing Yeast Vectors Effective for Intergeneric Gene Transfer," *Agric. Biol. Chem.* 50(6):1503–1512 (1986).

Wood, W.A. et al., "Ribitol and $_D$-Arabitol Utilization by *Aerobactor aerogenes*," *J. Biol. Chem.* 236(8):2190–2195 (Aug. 1961).

Bailey, "Toward a Science of Metabolic Engineering", Science, vol. 252, pp. 1668–1675. Jun. 21, 1991.

MANUFACTURING OF XYLITOL USING RECOMBINANT MICROBIAL HOSTS

CROSS REFERENCE TO RELATED APPLICATION

This application is a continuation, of application Ser. No. 08/110,672, filed Aug. 24, 1993, abandoned, which is a continuation-in-part application of U.S. Appl. No. 07/973,325, filed Nov. 5, 1992, abandoned.

BACKGROUND OF THE INVENTION

1. Field of the Invention

The present invention relates generally to methods of using genetically modified microorganisms for the manufacture of useful chemical compounds (metabolic engineering) and more specifically to constructing microbial strains by genetic manipulation that are capable of converting readily available carbon sources, such as D-glucose, into a more valuable product, for example, xylitol.

2. Related Art

Xylitol is a chemical compound of a considerable value as a special sweetener. It is approximately as sweet as sucrose, non-toxic, and non-cariogenic.

Currently, xylitol is produced by chemical hydrogenation of D-xylose. D-xylose is obtained from hydrolysates of various plant materials where it is always present in a mixture with other pentoses and hexoses. Purification of xylose and also xylitol presents therefore a significant problem. A number of processes of this type are known. U.S. Pat. Nos. 3,784,408, 4,066,711, 4,075,406, and 4,008,285 can be mentioned as examples.

The reduction of D-xylose into xylitol can also be achieved in a microbiological process using either strains isolated from nature (Barbosa, M. F. S. et al., *J. Industrial Microbiol.* 3: 241–251 (1988)) or genetically engineered strains (Hallborn, J. et al., *Biotechnology* 9: 1090–1095 (1991)). However, obtaining the substrate, D-xylose, in a form suitable for yeast fermentation is also a considerable problem because inexpensive xylose sources such as sulphite liquor from pulp and paper processes contain impurities which inhibit yeast growth.

An attractive alternative method for the manufacture of xylitol would be obtaining it by fermentation of a cheap and readily available substrate, such as D-glucose. However, no microorganisms are known that produce xylitol in significant amounts during one-step fermentation of any common carbon sources other than D-xylose and D-xylulose, both of which are structurally very closely related to xylitol.

On the other hand, many microorganisms, especially osmophilic yeasts, for example *Zygosaccharomyces rouxii*, *Candida polymorpha*, and *Torulopsis candida*, produce significant amounts of a closely related pentitol, D-arabitol, from D-glucose (Lewis D. H. & Smith D. C., *New Phytol.* 66: 143–184 (1967)). Using this property of osmophilic yeasts, H. Onishi and T. Suzuki developed a method for converting D-glucose into xylitol by three consecutive fermentations (*Appl. Microbiol.* 18: 1031–1035 (1969)). In this process, D-glucose was first converted into D-arabitol by fermentation with an osmophilic yeast strain. Second, the D-arabitol was oxidized into D-xylulose in a fermentation with *Acetobacter suboxydans*. Finally, the D-xylulose was reduced to xylitol in the third fermentation using one of many yeast strains capable of reducing D-xylulose into xylitol.

An obvious disadvantage of this method is that it involves three different fermentation steps, each taking from 2 to 5 days; further additional steps like sterilization and cell removal are also needed, thus increasing processing costs. The yield of the step fermentation process is low and the amount of by-products is high. Thus, a need still exists for methods for the economical production of xylitol in microbial systems from readily available substrates.

SUMMARY OF THE INVENTION

The present invention provides methods for constructing recombinant hosts, and the recombinant hosts constructed thereby, such hosts being capable of producing xylitol when grown on carbon sources other than D-xylulose or D-xylose, and other than polymers or oligomers or mixtures thereof. The carbon sources used by the hosts of the invention are inexpensive and readily available. The microorganisms of the invention are also capable of secreting the synthesized xylitol into the culture medium. This goal is achieved through modification of the metabolism of a desired microorganism, preferably a naturally occurring yeast microorganism, by introducing and expressing desired heterologous genes. This goal is also achieved by further modification of the metabolism of such desired microorganism, so as to overexpress and/or inactivate the activity or expression of certain genes homologous to such microorganism in its native state.

Therefore, it is an object of the invention to provide a method for the production of xylitol, such method utilizing a new and novel microbe strain, a recombinant host, also herein termed a genetically engineered microorganism, as the producer of such xylitol, such genetically engineered microorganism producing such xylitol either de novo or in enhanced amounts when compared the native unengineered microorganism.

It is a further object of the invention to provide a method for the production of xylitol, such method utilizing a novel metabolic pathway that has been engineered into a microorganism and which results in the de novo or enhanced production of xylitol by such microorganism.

It is a further object of the invention to provide a method for the production of xylitol, such method utilizing a novel metabolic pathway as above, and such pathway modifying the pathway of D-arabitol biosynthesis and/or metabolism, such pathway being modified so that the microorganism now produces xylitol from fermentation of carbon sources that the unmodified host utilizes for D-arabitol biosynthesis.

It is a further object of the invention to provide a method for the production of xylitol, such method utilizing the altered D-arabitol pathway above, and such pathway being altered either by the extension of the preexisting pathway for D-arabitol biosynthesis (with additional steps for D-arabitol utilization) or by the substitution of one or more steps of the D-arabitol pathway with similar steps leading to the formation of xylitol.

It is a further object of the invention to provide a method for the production of xylitol, such method utilizing the altered D-arabitol biosynthesis pathway above, and such pathway being altered by extending the pre-existing D-arabitol pathway by the introduction and overexpression of the genes coding for D-xylulose-forming D-arabitol dehydrogenase (EC 1.1.1.11) and xylitol dehydrogenase (EC 1.1.1.9) into an D-arabitol-producing microorganism.

It is a further object of the invention to provide a method for the production of xylitol using a novel microorganism as above, such method utilizing the altered D-arabitol biosynthesis pathway above, and such pathway being altered further, by inactivating, using chemically induced mutagenesis or gene disruption, the gene coding for transketolase (EC 2.2.1.1) or the gene coding for D-xylulokinase (EC 2.7.1.17) in such microorganism.

It is a further object of the invention to provide a method for the production of xylitol using a novel microorganism as above, such method utilizing a genetically-engineered altered overexpression of the genes coding for the enzymes of the oxidative branch of the pentose-phosphate pathway, and specifically D-glucose-6-phosphate dehydrogenase (EC 1.1.1.49) and/or 6-phospho-D-gluconate dehydrogenase (EC 1.1.1.44) in such microorganism.

It is a further object of the invention to provide a method for the production of xylitol using a novel microrganism as above, such method utilizing a genetically-engineered altered overexpression of the genes coding for the enzymes of the oxidative branch of the pentose-phosphate pathway, as well as the D-ribulose-5-phosphate epimerase gene (EC 5.1.3.1).

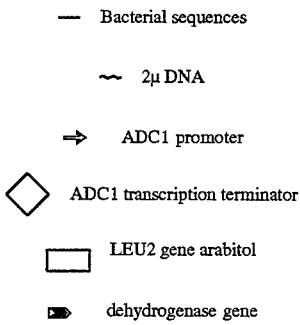

— Bacterial sequences

∼ 2μ DNA

→ ADC1 promoter

◊ ADC1 transcription terminator

▭ LEU2 gene arabitol

▶ dehydrogenase gene

Figure 3:
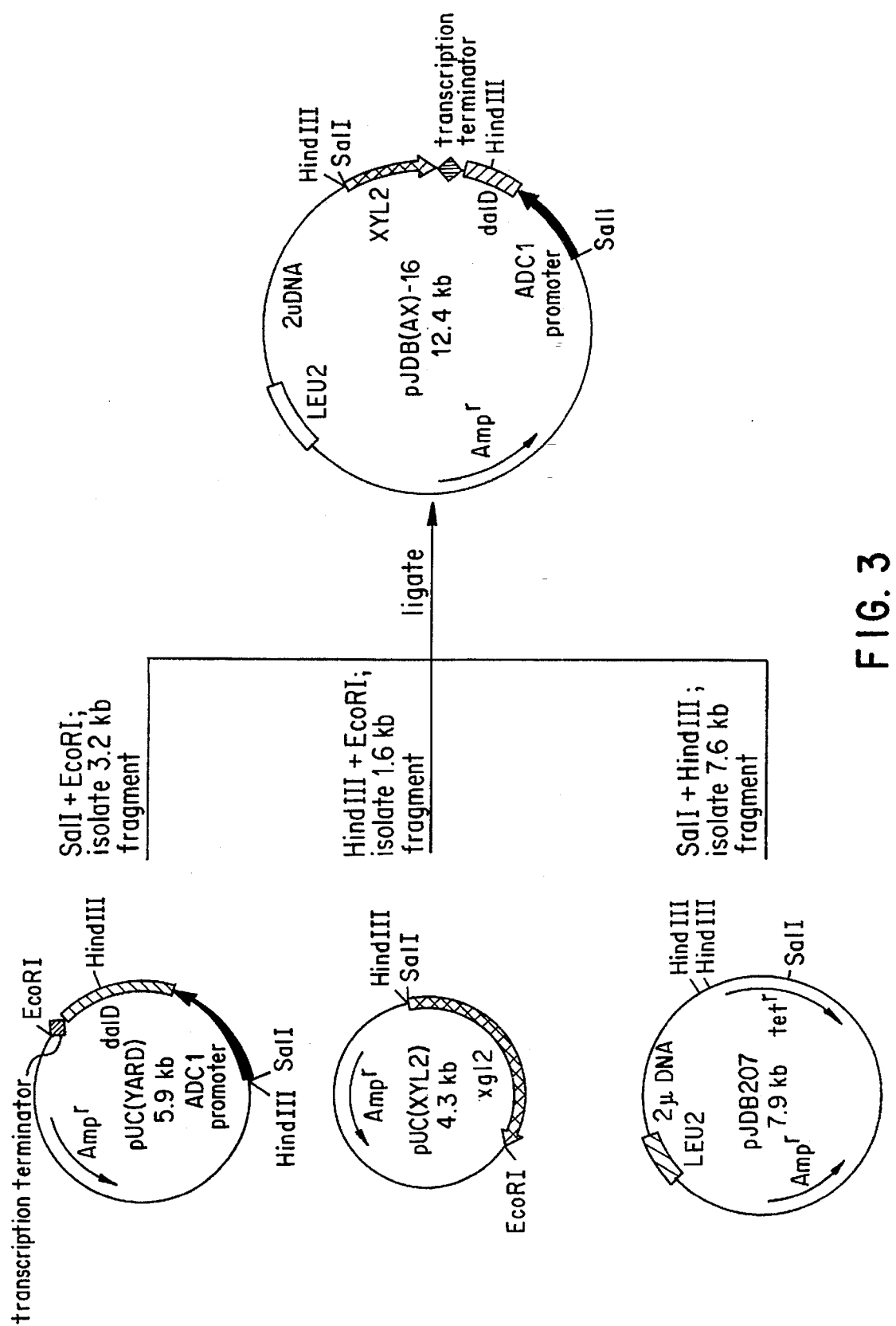

FIG. 3 shows the construction of plasmid pJDB(AX)-16. XYL2 is the xylitol dehydrogenase gene from *Pichia stipitis*. daID is the D-arabitol dehydrogenase gene. ADCI is the transcriptional regulation area (promoter) of the ADCI gene that precedes and is operably linked to the daID coding sequence. The symbols are not the same as in FIG. 4. On the plasmid diagrams, the single line (−) indicates bacterial sequences and 2 μm DNA where noted; the closed arrow indicates the ADC1 promoter; the shaded diamond (♦) indicates the ADCI transcriptional terminator; the rectangular block indicates the LEU2 marker gene; the hatched arrow indicates the XYL2 gene; and the blocked rectangle indicates the daID gene.

Figure 4:
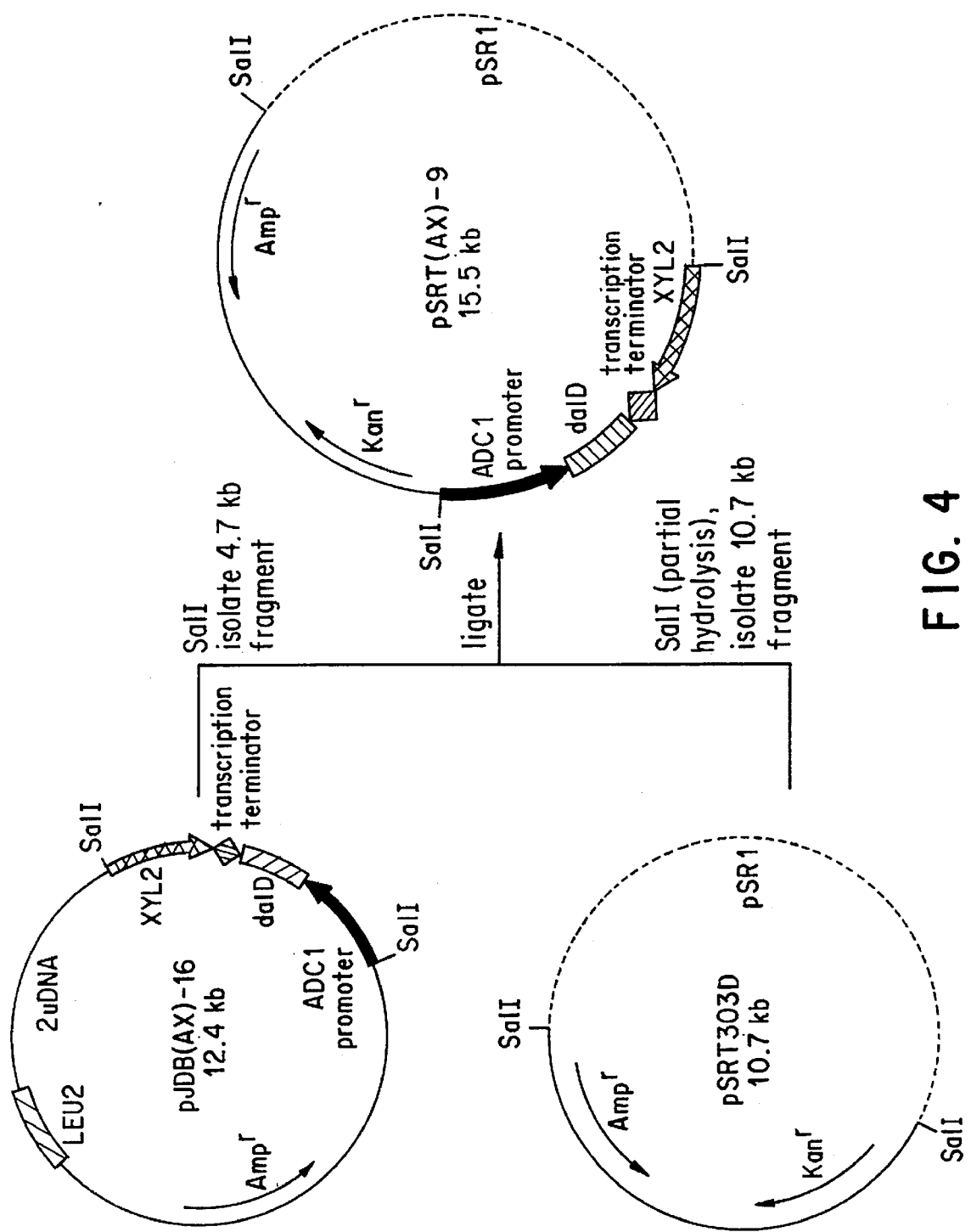

FIG. 4 shows the construction of the *E. coli-Z. rouxii* shuttle vector pSRT(AX)-9. The symbols are as in FIG. 3.

Figure 5:
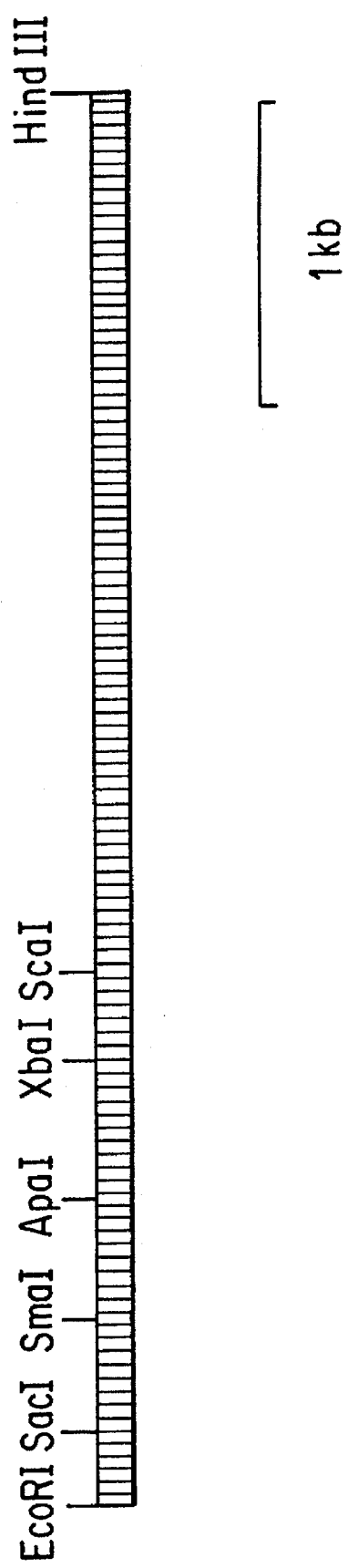

FIG. 5 shows the restriction map of the cloned *T. candida* rDNA fragment.

Figure 6:
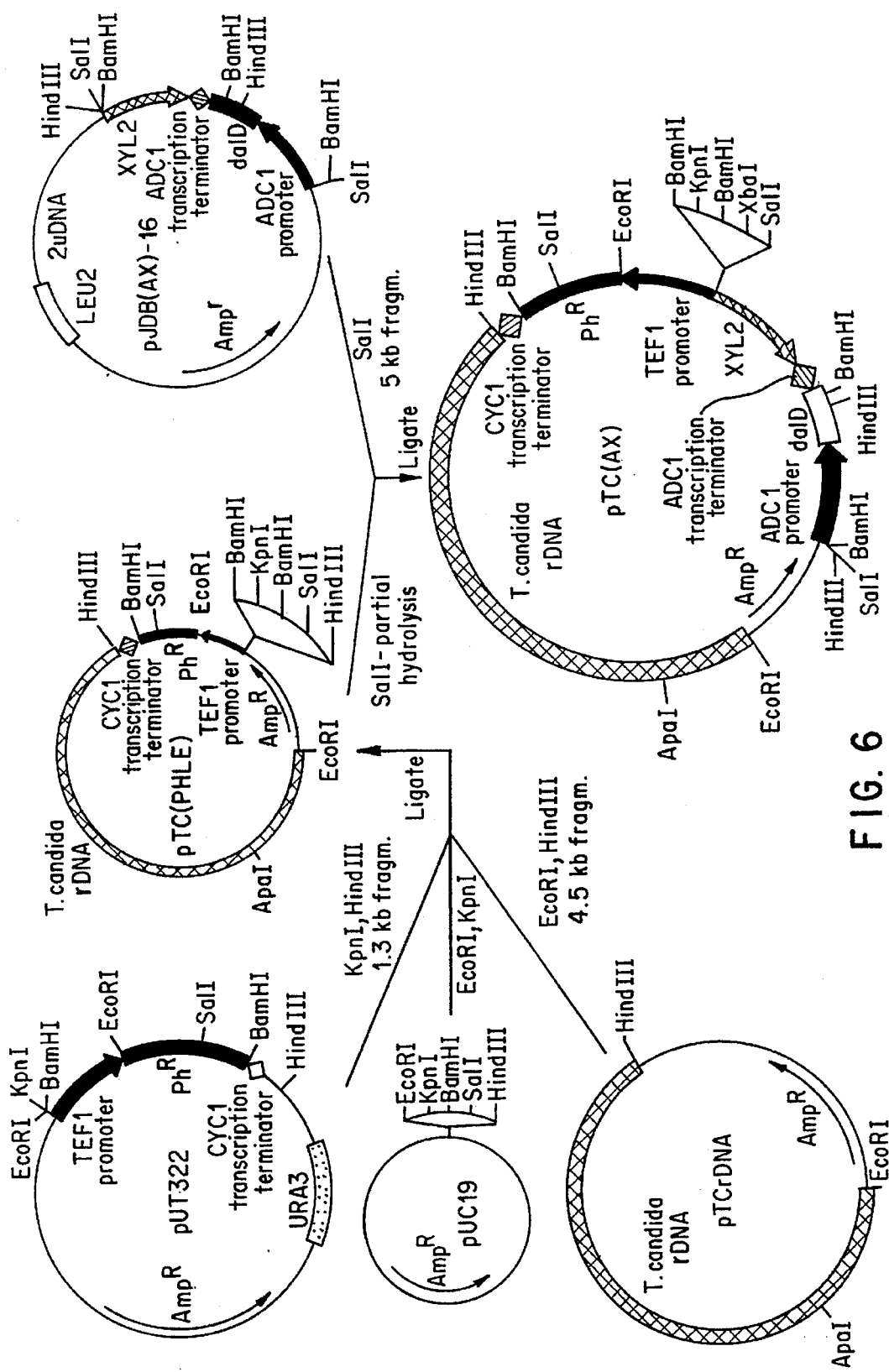

FIG. 6 shows the construction of the plasmid pTC(AX).

Figure 7:
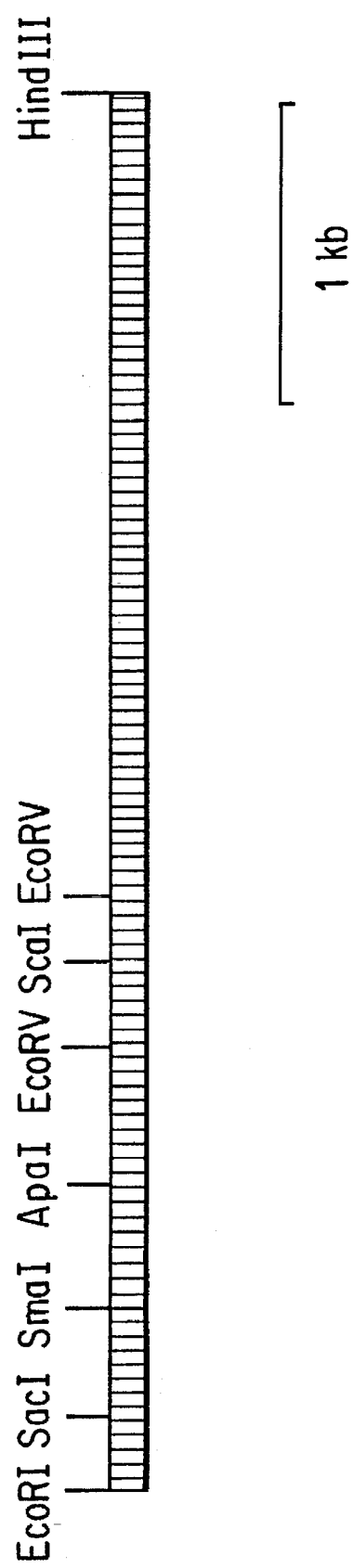

FIG. 7 shows the restriction map of the cloned *T. candida* rDNA fragment.

Figure 7A:
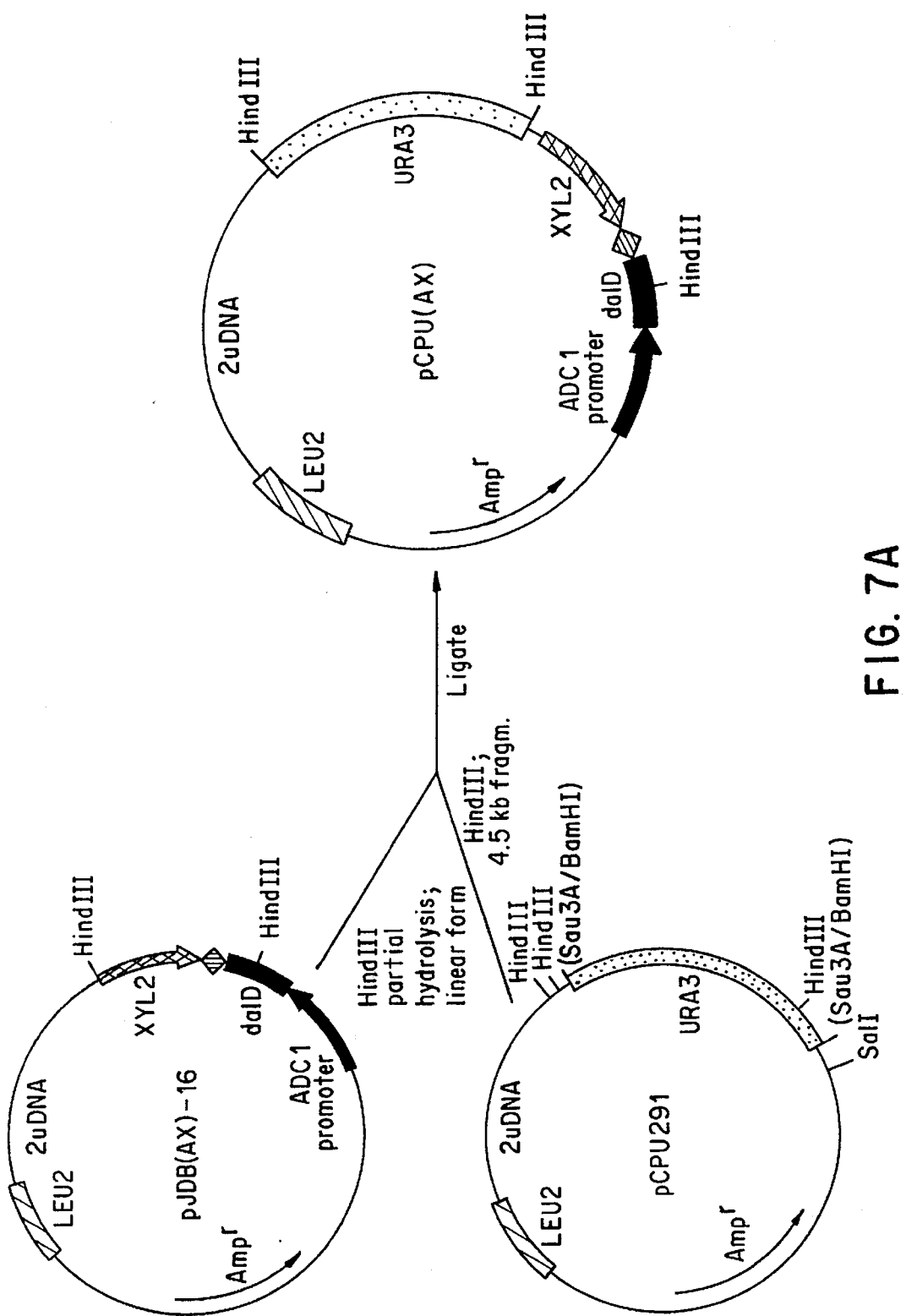

FIG. 7a shows the construction of the plasmid pCPU (AX).

Figure 8:
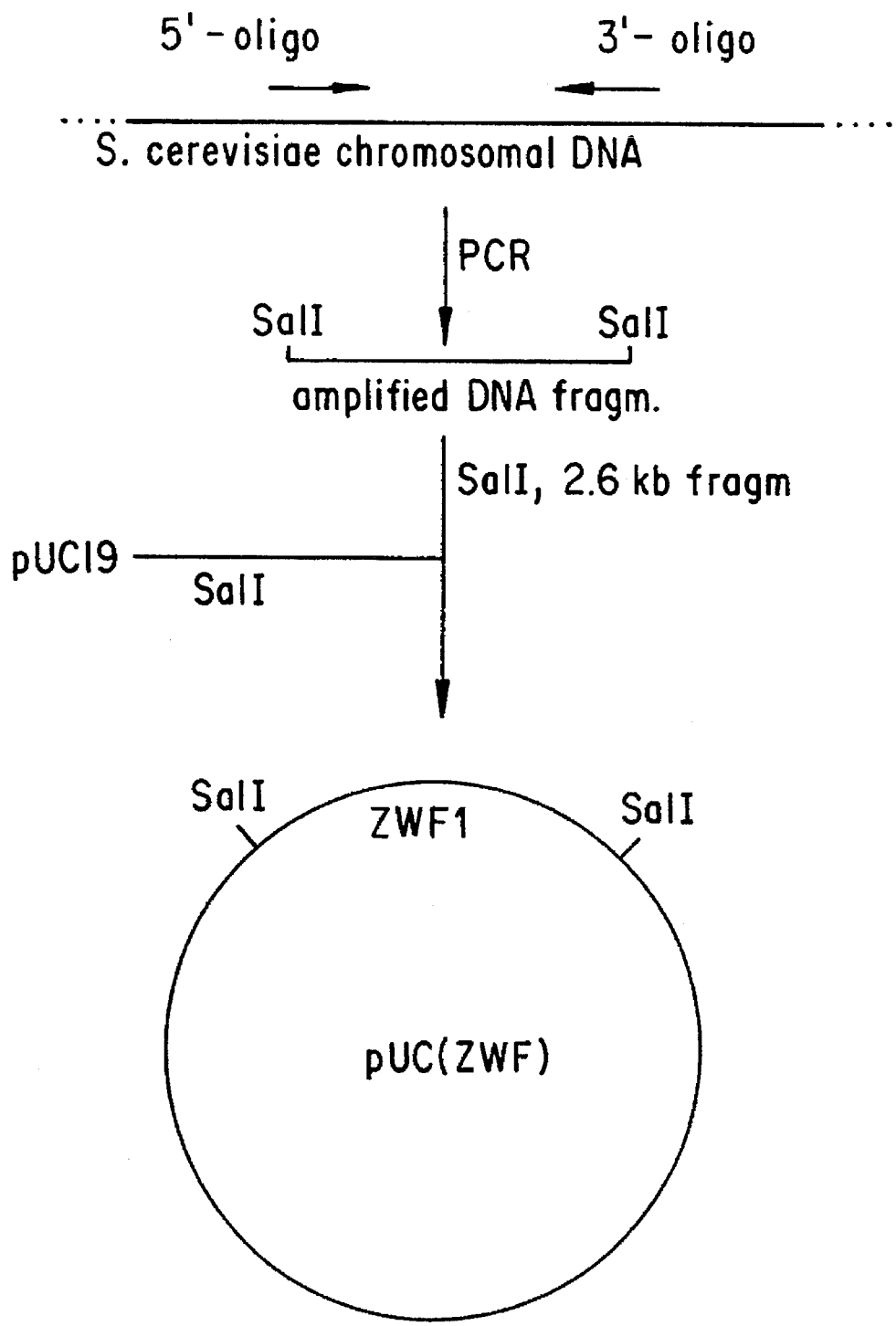

FIG. 8 shows the cloning of the ZWF1 and gnd gene.

Figure 8A:
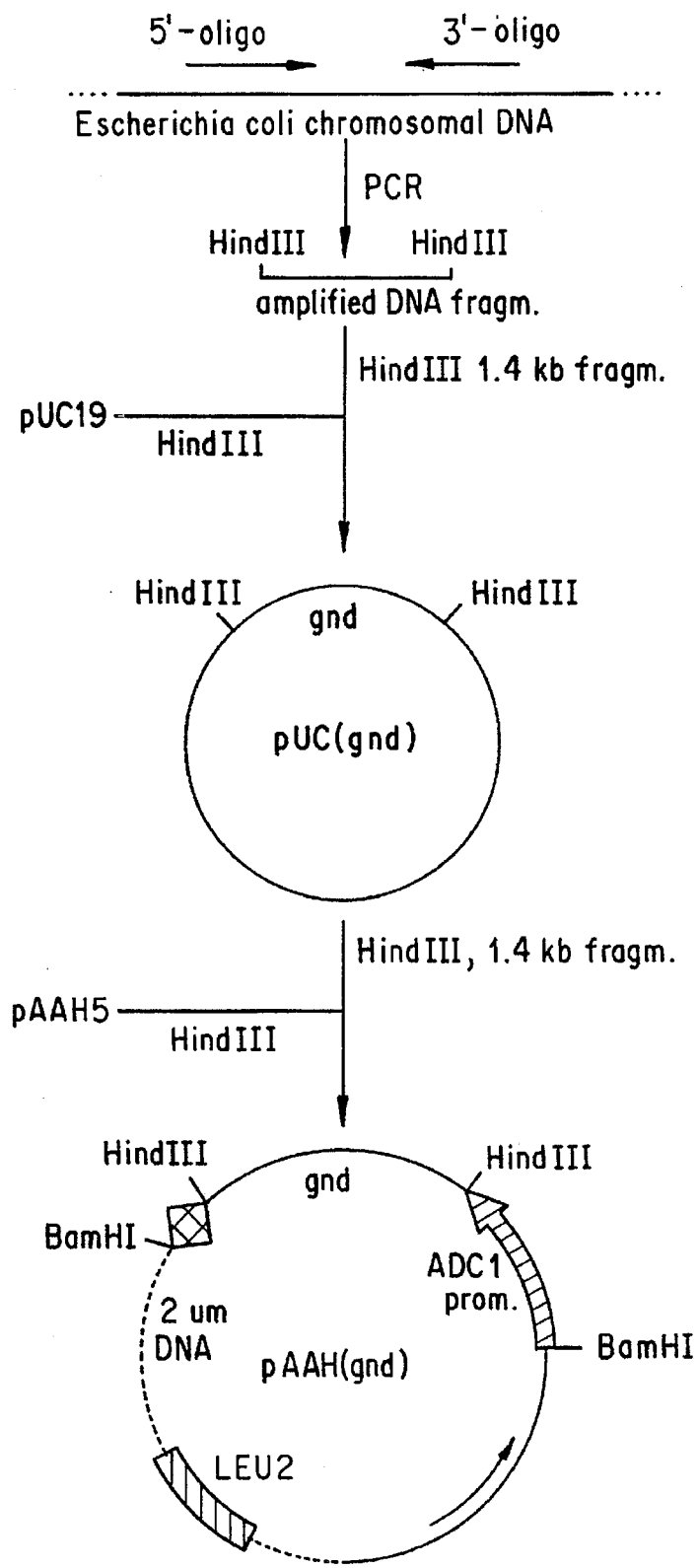

FIG. 8a shows the construction of the PAAH(gnd) plasmid.

Figure 9:
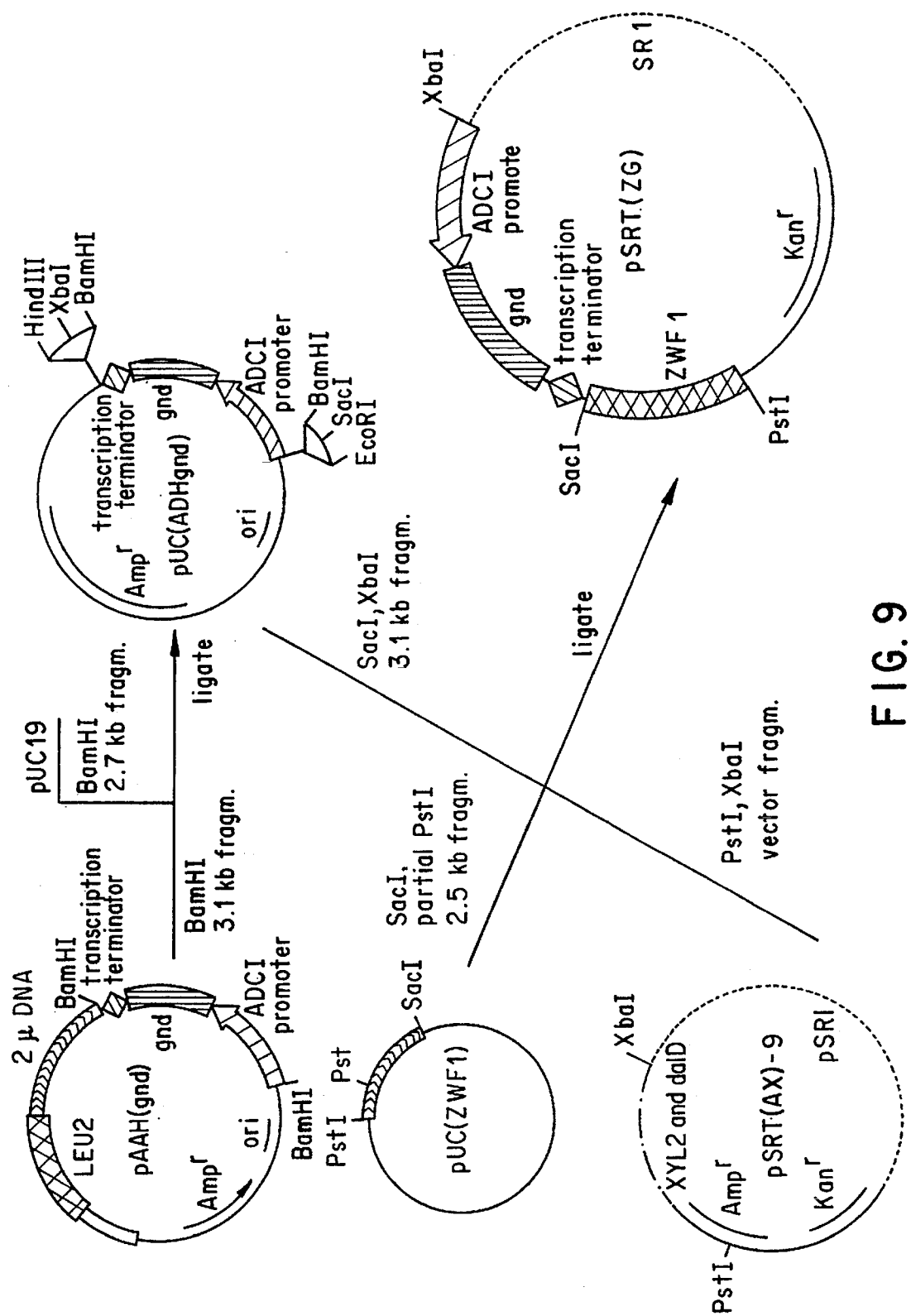

FIG. 9 shows the construction of plasmid pSRT(ZG).

Figure 10:
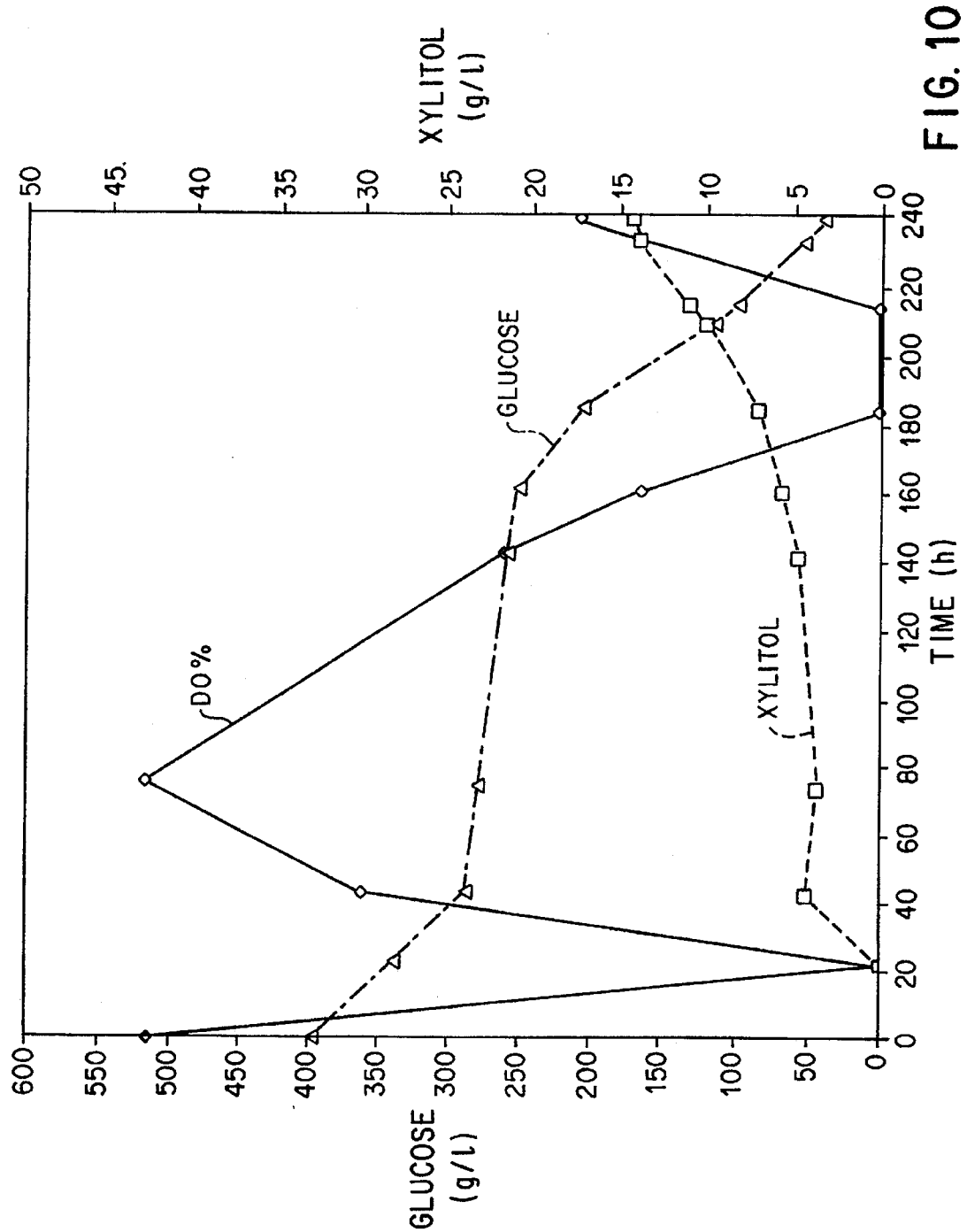

FIG. 10 shows the cultivation of the strain *Z. rouxii* ATCC 13356 [pSRT(AX)-09] in a fermentor.

Figure 11:
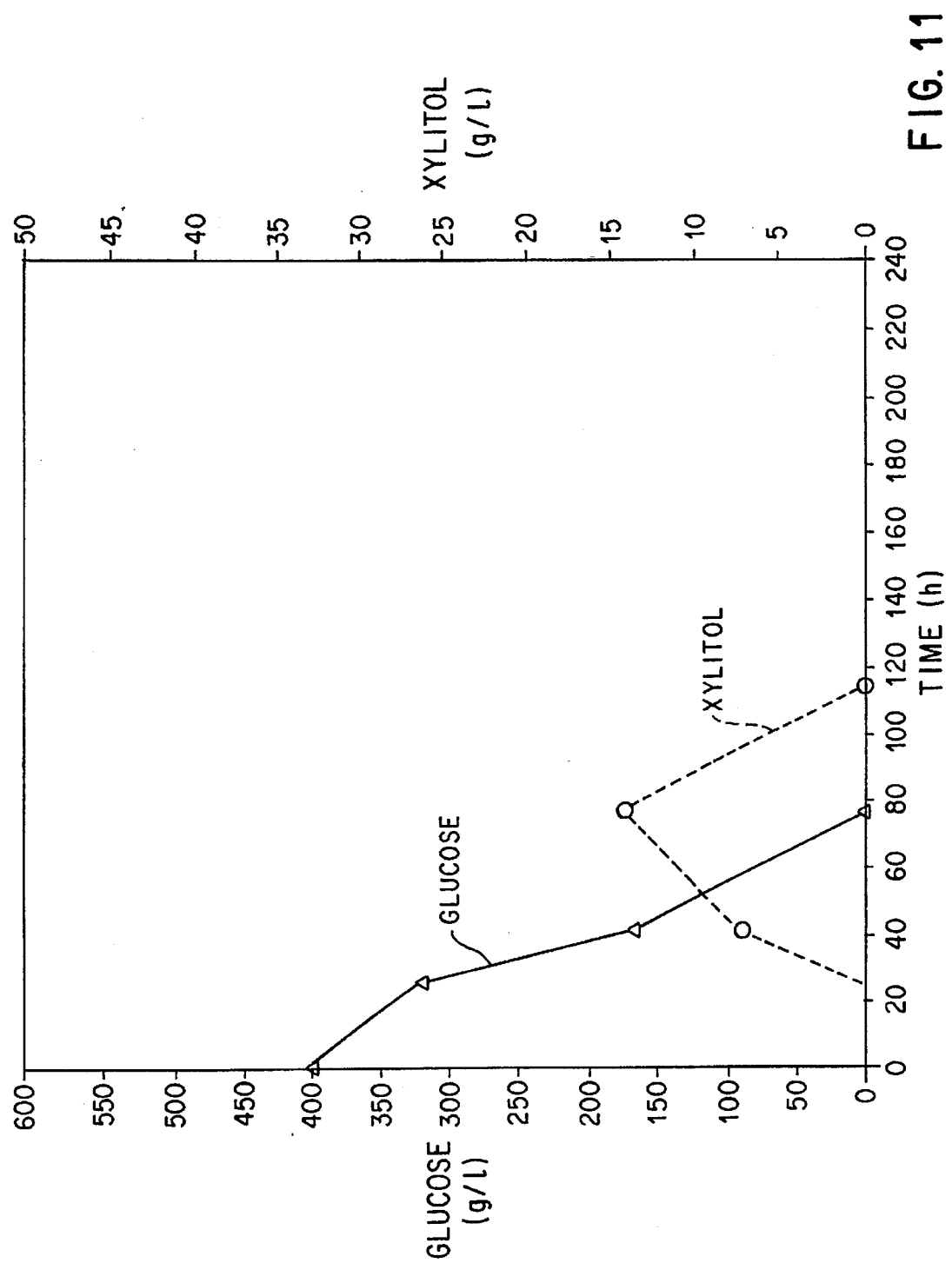

FIG. 11 shows the cultivation of the mutant derived from strain *Z. rouxii* ATCC 13356 [pSRT(AX)-9] in a fermentor.

DETAILED DESCRIPTION OF THE PREFERRED EMBODIMENTS

I. Definitions

In the description that follows, a number of terms used in recombinant DNA technology are extensively utilized. In order to provide a clear and consistent understanding of the specification and claims, including the scope to be given such terms, the following definitions are provided.

Carbon source other than xylose or xylulose. As used herein, by a "carbon source other than D-xylose and D-xylulose" is meant a carbon substrate for xylitol production other than D-xylose and D-xylulose or polymers or oligomers or mixtures thereof (such as xylan and hemicellulose). The carbon source preferably supports growth of the generically engineered microbial hosts of the invention, and fermentation in yeast hosts. Many cheap and readily available compounds can be used as carbon sources for the production of xylitol in the microbial hosts of the present invention, including D-glucose, and various D-glucose-containing syrups and mixtures of D-glucose with other sugars. Other sugars assimilable by the hosts of the invention, including yeast and fungi, such as various aldo- and ketohexoses (for example, D-fructose, D-galactose, and D-mannose), and oligomers and polymers thereof (for example, sucrose, lactose, starch, inulin and maltose) are intended to be included in this term. Pentoses other than xylose and xylulose and non-carbohydrate carbon sources such as glycerol, ethanol, various plant oils or hydrocarbons (preferably n-alkanes containing 14–16 carbon atoms) are also intended to be included in this term. The spectrum of carbon sources useful as substrates for the production of xylitol by the hosts of the present invention will vary depending on the microbial host. For example, glucose and glucose-containing syrups are the preferred carbon source for xylitol production with the genetically manipulated *Zygosaccharomyces rouxii* of the invention, while n-alkanes, preferably having 14–16 carbon atoms, are the preferred carbon source for modified *Candida tropicalis* strains.

Gene. A DNA sequence containing a template for a RNA polymerase. The RNA transcribed from a gene may or may not code for a protein. RNA that codes for a protein is termed messenger RNA (mRNA) and, in eukaryotes, is transcribed by RNA polymerase II. A gene containing a RNA polymerase II template (as a result of a RNA polymerase II promoter) wherein a RNA sequence is transcribed which has a sequence complementary to that of a specific mRNA, but is not normally translated can also be constructed. Such a gene construct is herein termed an "antisense RNA gene"

and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by, for example, reverse transcription of mRNA, thus lacking intervening sequences (introns). Genes clones from genomic DNA will generally contain introns.

Cloning vehicle. A plasmid or phage DNA or other DNA sequence which is able to carry genetic information, specifically DNA, into a host cell. A cloning vehicle is often characterized by one or a small number of endonuclease recognition sites at which such DNA sequences can be cut in a determinable fashion without loss of an essential biological function of the vehicle, and into which a desired DNA can be spliced in order to bring about its cloning into the host cell. The cloning vehicle can further contain a marker suitable for use in the identification of cells transformed with the cloning vehicle, and origins of replication that allow for the maintenance and replication of the vehicle in one or more prokaryotic or eukaryotic hosts. Markers, for example, are tetracycline resistance or ampicillin resistance. The word "vector" is sometimes used for "cloning vehicle." A "plasmid" is a cloning vehicle, generally circular DNA, that is maintained and replicates autonomously in at least one host cell.

Expression vehicle. A vehicle or vector similar to a cloning vehicle but which supports expression of a gene that has been cloned into it, after transformation into a host. The cloned gene is usually placed under the control of (i.e., operably linked to) certain control sequences such as promoter sequences, that can be provided by the vehicle or by the recombinant construction of the cloned gene. Expression control sequences will vary depending on whether the vector is designed to express the operably linked gene in a prokaryotic or eukaryotic host and can additionally contain transcriptional elements such as enhancer elements (upstream activation sequences) and termination sequences, and/or translational initiation and termination sites.

Host. A host is a cell, prokaryotic or eukaryotic, that is utilized as the recipient and carrier of recombinant material.

Host of the Invention. The "host of the invention" is a microbial host that does not naturally produce xylitol in significant amounts during fermentation from common carbon sources other than D-xylose or D-xylulose, or polymers or oligomers or mixtures thereof, but has been engineering to do so according to the methods of the invention. By a "significant amount" is meant an amount which is suitable for isolation of xylitol in pure form or an amount that can be reliably measured by the analytical methods normally used for the analysis of carbohydrates in the microbial fermentation broth.

Arabitol Dehydrogenase. There are two types of D-arabitol dehydrogenases: D-xylulose-forming (EC 1.1.1.11) and D-ribulose-forming. D-ribulose-forming dehydrogenases are found in wild type yeasts and fungi. D-xylulose-forming arabitol dehydrogenases are known only in bacteria. Unless otherwise stated, it is the D-xylulose-forming arabitol dehydrogenase that is intended herein and referred to herein as arabitol dehydrogenase.

Oxidative Branch of the Pentose-Phosphate Pathway. By the "oxidative branch of the pentose-phosphate pathway" is meant to include that part of the pentose-phosphate shunt that catalyzes oxidative reactions, such as those reactions catalyzed by D-glucose-6-phosphate dehydrogenase (EC 1.1.1.49) and 6-phospho-D-gluconate dehydrogenase (EC 1.1.1.44), and that utilizes hexose substrates to form pentose phosphates. The "non-oxidative" part of the pentose-phosphate pathway (which also catalyzes the net formation of ribose from D-glucose) is characterized by non-oxidative isomerizations such as the reactions catalyzed by ribose-5-phosphate isomerase, D-ribulose-5-phosphate-3-epimerase and transaldolase. See *Biological Chemistry*, H. R. Mahler & E. H. Cordes, Harper & Row, publishers, New York, 1966, pp. 448–454.

Functional Derivative. A "functional derivative" of a protein or nucleic acid, is a molecule that has been chemically or biochemically derived from (obtained from) such protein or nucleic acid and which retains a biological activity (either functional or structural) that is a characteristic of the native protein or nucleic acid. The term "functional derivative" is intended to include "fragments," "variants," "analogues," or "chemical derivatives" of a molecule that retain a desired activity of the native molecule.

As used herein, a molecule is said to be a "chemical derivative" of another molecule when it contains additional chemical moieties not normally a part of the molecule. Such moieties can improve the molecule's solubility, absorption, biological half life, etc. The moieties can decrease the toxicity of the molecule, or eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Fragment. A "fragment" of a molecule such as a protein or nucleic acid is meant to refer to a portion of the native amino acid or nucleotide genetic sequence, and in particular the functional derivatives of the invention.

Variant or Analog. A "variant" or "analog" of a protein or nucleic acid is meant to refer to a molecule substantially similar in structure and biological activity to either the native molecule, such as that encoded by a functional allele.

II. Construction of Metabolic Pathways for Xylitol Biosynthesis

According to the invention, the native metabolic pathways of a microbial host are manipulated so as to decrease or eliminate the utilization of carbon into purposes other than xylitol production. All of the hosts of the invention produce xylitol in one fermentation step. In one embodiment, a hosts of the invention can possess xylitol dehydrogenase (EC 1.1.1.9) activity sufficient for xylitol production. However, as described below, in those hosts wherein it is desired to overproduce xylitol dehydrogenase activity, recombinant genes encoding xylitol dehydrogenase can be transformed into the host cell.

In the practical realization of the invention, all of the hosts of the invention are characterized by the ability to synthesize xylitol from structurally unrelated carbon sources such as D-glucose and not just from D-xylose and/or D-xylulose. The hosts of the invention are also capable of secreting the synthesized xylitol into the medium.

Specifically, in the exemplified and preferred embodiments, the hosts of the invention are characterized by one of two pathways. First, a pathway in which arabitol is an intermediate in xylitol formation and second, a pathway in which xylulose-5-phosphate is directed into xylitol formation through dephosphorylation and reduction reactions. Accordingly, the hosts of the invention are characterized by at least one of the following genetic alterations:

(1) a gene encoding a protein possessing D-xylulose-forming D-arabitol dehydrogenase activity (EC 1.1.1.11)

has been cloned into the host-thus providing for the conversion of D-arabitol to D-xylulose (characteristic of pathway I); and/or (2) the native host gene encoding transketolase activity has been inactivated (characteristic of pathway II).

In addition a variety of further modifications to the hosts can be performed, so as to enhance the xylitol producing capabilities of such hosts. For example, the hosts as described in (1) and (2) can be further modified such that:

(3) a gene encoding a protein possessing xylitol dehydrogenase (EC 1.1.1.9) activity has been cloned into the host;

(3) the native host gene encoding D-xylulokinase (EC 2.7.1.17) has been inactivated;

(4) a gene encoding a protein possessing D-glucose-6-phosphate dehydrogenase (EC 1.1.1.49) activity has been cloned into the host;

(4) a gene encoding a protein possessing 6-phospho-D-gluconate dehydrogenase (EC 1.1.1.44) activity has been cloned into the host;

(5) a gene encoding a protein possessing D-ribulose-5-phosphate-3-epimerase (EC 5.1.3.1) activity has been cloned into the host;

In a preferred embodiment, the hosts of the invention possess more than one of the above-described genetic alterations. For example, in a preferred embodiment, carbon flows from D-arabitol "directly to" (that is, in one step) D-xylulose, and from D-xylulose "directly to" xylitol. Accordingly, in such embodiment, the host of the invention has been altered such that a gene encoding a protein possessing D-xylulose-forming D-arabitol dehydrogenase activity and a gene encoding a xylitol dehydrogenase (EC 1.1.1.9) have been cloned into the host. It should be noted that while, in many embodiments, D-arabitol is internally synthesized from other carbon sources by the hosts of the invention, D-arabitol could also be externally added directly to the medium.

In another preferred embodiment, the xylitol biosynthesis pathway does not incorporate arabitol as an intermediate. Rather, the carbon flow is from D-xylulose-5-phosphate to D-xylulose further to xylitol. When D-glucose is used as the carbon source, the flow of carbon would be through the oxidative portion of the pentose phosphate pathway, from D-glucose to D-glucose-6-phosphate to 6-phospho-D-gluconate to D-ribulose-5-phosphate. The D-ribulose-5-phosphate would further epimerized to D-xylulose-5-phosphate, dephosphorylated to D-xylulose and reduced to xylitol. Accordingly, a host of the invention for utilization of this embodiment would include a host in which:

(a1) a gene encoding a protein possessing D-glucose-6-phosphate dehydrogenase (EC 1.1.1.49) activity has been cloned into the host or the native gene of the host is overexpressed; and/or (a2) a gene encoding a protein possessing 6-phospho-D-gluconate dehydrogenase (EC 1.1.1.44) activity has been cloned into the host or the native gene of the host is overexpressed; and/or (a3) a gene encoding a protein possessing D-ribulose-5-phosphate-3-epimerase activity has been cloned into the host or the native gene of the host is overexpressed; and/or (a4) a gene encoding a protein possessing xylitol dehydrogenase (EC 1.1.1.9) activity has been cloned into the host or the native gene of the host is overexpressed;

(b) the native transketolase gene has been inactivated; and/or (c) the native host gene encoding xylulokinase (EC 2.7.1.17) activity has been inactivated.

The dephosphorylation step (D-xylulose-phosphate to D-xylulose conversion) is the only step catalyzed by an enzyme that has not been characterized in pure form. However, the enzyme activity responsible for the similar step (D-ribulose-5-phosphate to D-ribulose) in the native D-arabitol-forming pathway of osmophilic yeast was previously shown to be non-specific and capable also of catalyzing the dephosphorylation of xylulose-5-phosphate (Ingram, J. M. and W. A. Wood, *J. Bacteriol.* 89: 1186–1194 (1965)). The mutation of transketolase and overexpression of the two dehydrogenases of the oxidative pentose phosphate pathway serve a dual purpose. First, they can increase the efficiency of pathway I by increasing the amount of ribulose-5-phosphate in the cell and consequently the production of arabitol and xylitol. Secondly, the overaccumulation of xylulose-5-phosphate which is necessary for the operation of pathway II should also result from the same combination of modifications.

Therefore, methods utilizing the naturally occurring pathway leading to the formation of D-arabitol from various carbon sources and extending this pathway by two more reactions to convert D-arabitol into xylitol are not the only possible pathway within the invention. Other pathways leading to xylitol as a final metabolic product and not involving D-arabitol as an intermediate can be constructed. Thus, a pathway to xylitol from D-ribulose-5-phosphate, can be realized through more than one chain of reactions. D-ribulose-5-phosphate can efficiently be converted to D-xylulose-5-phosphate by D-ribulose-5-phosphate-3-epimerase and if further conversion of D-xylulose-5-phosphate is prevented by a mutation in the transketolase gene, the accumulated D-xylulose-5-phosphate can be dephosphorylated by the same non-specific phosphatase as D-ribulose-5-phosphate (Ingram, J. M. et al., *J. Bacteriol.* 89: 1186–1194 (1965)) and reduced into xylitol by xylitol dehydrogenase. Realization of this pathway can further require the inactivation of D-xylulokinase gene in order to minimize the energy loss due to the futile loop: D-xylulose-5-phosphate→D*xylulose→D-xylulose-5-phosphate. An additional genetic change—introduction and (over)-expression of the D-ribulokinase gene (EC 2.7.1.47) could minimize simultaneous D-arabitol production by such strains by trapping the D-ribulose produced by the unspecific phosphatase. The D-ribulose will be converted back into the D-ribulose-5-phosphate and further into D-xylulose-5-phosphate.

III. Construction of the Hosts of the Invention

The process for genetically engineering the hosts of the invention, according to the invention, is facilitated through the isolation and partial sequencing of pure protein encoding an enzyme of interest or by the cloning of genetic sequences which are capable of encoding such protein with polymerase chain reaction technologies; and through the expression of such genetic sequences. As used herein, the term "genetic sequences" is intended to refer to a nucleic acid molecule (preferably DNA). Genetic sequences which are capable of encoding a protein are derived from a variety of sources. These sources include genomic DNA, cDNA, synthetic DNA, and combinations thereof. The preferred source of genomic DNA is a yeast genomic library. The preferred source of the cDNA is a cDNA library prepared from yeast mRNA grown in conditions known to induce expression of the desired mRNA or protein.

The cDNA of the invention will not include naturally occurring introns if the cDNA was made using mature mRNA as a template. The genomic DNA of the invention may or may not include naturally occurring introns. Moreover, such genomic DNA can be obtained in association with the 5' promoter region of the gene sequences and/or with the 3' transcriptional termination region. Further, such genomic DNA can be obtained in association with the genetic sequences which encode the 5' non-translated region of the mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, can be retained and employed for transcriptional and translational regulation. Genomic DNA can be extracted and purified from any host cell, especially a fungal host, which naturally expresses the desired protein by means well known in the art (for example, see *Guide to Molecular Cloning Techniques*, S. L. Berger et al., eds., Academic Press (1987)). Preferably, the mRNA preparation used will be enriched in mRNA coding for the desired protein, either naturally, by isolation from cells which are producing large amounts of the protein, or in vitro, by techniques commonly used to enrich mRNA preparations for specific sequences, such as sucrose gradient centrifugation, or both.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding a desired protein or its functional derivatives can be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., (Maniatis, T. et al., *Molecular Cloning (A Laboratory Manual)*, Cold Spring Harbor Laboratory, second edition, 1988) and are well known in the art.

Libraries containing sequences coding for the desired gene can be screened and the desired gene sequence identified by any means which specifically selects for a sequence coding for such gene or protein such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for a certain protein which can be used to identify clones to this protein can be designed from the knowledge of the amino acid sequence of the protein or from the knowledge of the nucleic acid sequence of the DNA encoding such protein or a related protein. Alternatively, antibodies can be raised against purified forms of the protein and used to identify the presence of unique protein determinants in transformants that express the desired cloned protein. The sequence of amino acid residues in a peptide is designated herein either through the use of their commonly employed three-letter designations or by their single-letter designations. A listing of these three-letter and one-letter designations can be found in textbooks such as *Biochemistry*, Lehninger, A., Worth Publishers, New York, N.Y. (1970). When the amino acid sequence is listed horizontally, unless otherwise stated, the amino terminus is intended to be on the left end and the carboxy terminus is intended to be at the right end. Similarly, unless otherwise stated or apparent from the context, a nucleic acid sequence is presented with the 5' end on the left.

Because the genetic code is degenerate, more than one codon can be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which can be encoded by oligonucleotides having the lowest degree of degeneracy. This is preferably accomplished by identifying sequences that contain amino acids which are encoded by only a single codon.

Although occasionally an amino acid sequence can be encoded by only a single oligonucleotide sequence, frequently the amino acid sequence can be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code, one or more different oligonucleotides can be identified from the amino acid sequence, each of which would be capable of encoding the desired protein. The probability that a particular oligonucleotide will, in fact, constitute the actual protein encoding sequence can be estimated by considering abnormal base pairing relationships and the frequency with which a particular codon is actually used (to encode a particular amino acid) in eukaryotic cells. Using "codon usage rules," a single oligonucleotide sequence, or a set of oligonucleotide sequences, that contain a theoretical "most probable" nucleotide sequence capable of encoding the protein sequences is identified.

The suitable oligonucleotide, or set of oligonucleotides, which is capable of encoding a fragment of a certain gene (or which is complementary to such an oligonucleotide, or set of oligonucleotides) can be synthesized by means well known in the art (see, for example, *Synthesis and Application of DNA and RNA*, S. A. Narang, ed., 1987, Academic Press, San Diego, Calif.) and employed as a probe to identify and isolate a clone to such gene by techniques known in the art. Techniques of nucleic acid hybridization and clone identification are disclosed by Maniatis, T., et al., in: *Molecular Cloning, A Laboratory Manual*, Cold Spring Harbor Laboratories, Cold Spring Harbor, N.Y. (1982)), and by Hames, B. D., et al., in: *Nucleic Acid Hybridization, A Practical Approach*, IRL Press, Washington, D.C. (1985)). Those members of the above-described gene library which are found to be capable of such hybridization are then analyzed to determine the extent and nature of coding sequences which they contain.

To facilitate the detection of a desired DNA coding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label can be employed which provides for an adequate signal and has a sufficient half-life. If single stranded, the oligonucleotide can be radioactively labelled using kinase reactions. Alternatively, polynucleotides are also useful as nucleic acid hybridization probes when labeled with a non-radioactive marker such as biotin, an enzyme or a fluorescent group.

Thus, in summary, the elucidation of a partial protein sequence, permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a gene.

In an alternative way of cloning a gene, a library is prepared using an expression vector, by cloning DNA or, more preferably cDNA prepared from a cell capable of expressing the protein into an expression vector. The library is then screened for members which express the desired protein, for example, by screening the library with antibodies to the protein.

The above discussed methods are, therefore, capable of identifying genetic sequences which are capable of encoding a protein or biologically active or antigenic fragments of this protein. In order to further characterize such genetic sequences, and, in order to produce the recombinant protein, it is desirable to express the proteins which these sequences encode. Such expression identifies those clones which express proteins possessing characteristics of the desired protein. Such characteristics can include the ability to specifically bind antibody, the ability to elicit the production of antibody which are capable of binding to the native, non-recombinant protein, the ability to provide a enzymatic activity to a cell that is a property of the protein, and the ability to provide a non-enzymatic (but specific) function to a recipient cell, among others.

A DNA sequence can be shortened by means known in the art to isolate a desired gene from a chromosomal region that contains more information than necessary for the utilization of this gene in the hosts of the invention. For example, restriction digestion can be utilized to cleave the full-length sequence at a desired location. Alternatively, or in addition, nucleases that cleave from the 3'-end of a DNA molecule can be used to digest a certain sequence to a shortened form, the desired length then being identified and purified by gel electrophoresis and DNA sequencing. Such nucleases include, for example, Exonuclease III and Bat31. Other nucleases are well known in the art.

In the practical realization of the invention the osmophilic yeast Z. rouxii has been employed as a model. Z. rouxii is compatible with food production since it is traditionally used in Japan for the manufacture of soy sauce. The yeast has been described for instance in: *The Yeasts, A Taxonomic Study*, Kreger-van Rij (ed.), Elsevier Science publishers B. V., Amsterdam 3984, wherein this yeast is described on pages 462–465. Other D-arabitol-producing yeasts like *Candida polymorpha*, *Torulopsis candida*, *Candida tropicalis*, *Pichia farinosa*, *Torulaspora hansenii*, etc., as well as D-arabitol producing fungi like *Dendryphiella salina* or *Schizophyllum commune* can also be used as host organisms for the purposes of the present invention.

The enzymes oxidizing D-arabitol into D-xylulose (EC 1.1.1.11) are known to occur in bacteria but not in yeast or fungi. For the purposes of the present invention *Klebsiella terrigena* is the preferred source of the D-arabitol dehydrogenase (D-xylulose forming) gene since it is a nonpathogenic soil bacterium and it has a high inducible D-arabitol dehydrogenase activity. The *Klebsiella terrigena* strain Php1 used in the examples was obtained from K. Haahtela, Helsinki University. The isolation of the strain is described in Haahtela et al., *Appl. Env. Microbiol.* 45: 563–570 (1983)). The cloning of the D-arabitol dehydrogenase gene can be conveniently achieved by constructing a genetic library of the *K. terrigena* chromosomal DNA in a suitable vector, for instance well known, and commercially available, plasmid pUC19. This library is transformed into one of many *E. coli* strains which are able to utilize D-xylulose but not D-arabitol as a sole carbon source. *E. coli* strain SCS1 available from Stratagene is an example of a suitable strain. The transformants are then plated on a medium containing D-arabitol as a sole carbon source and the clones able to grow on this medium are isolated. The coding region of the *K. terrigena* D-arabitol dehydrogenase can be conveniently isolated in a form of 1.38 kb BclI-ClaI fragment and fused with appropriate promoter and transcription terminator sequences. The *Saccharomyces cerevisiae* ADCl promoter and transcription terminator are examples of transcriptional regulatory elements suitable for the purposes of the present invention when the yeast Z. *rouxii* is used as a host organism. The sequence of ADCl is available from GenBank.

Although the majority of yeasts and fungi possess the xylitol dehydrogenase (EC 1.1.1.9) gene, overexpression of the said gene will typically be necessary for the implementation of the present invention. The cloning of the *Pichia slipitis* XYL2 gene encoding xylitol dehydrogenase (EC 1.1.1.9) can conveniently be achieved by polymerase chain reaction technology using the published information on the nucleotide sequence of the XYL2 gene (Kötter et al., *Curr. Genet.* 18: 493–500 (1990)). The gene can be introduced into other yeast species without any modifications and expressed under control of its own promoter or the promoter can be exchanged for another strong yeast promoter.

Genetically stable transformants can be constructed with vector systems, or transformation systems, whereby a desired DNA is integrated into the host chromosome. Such integration can occur de novo within the cell or be assisted by transformation with a vector which functionally inserts itself into the host chromosome, for example, with phage, retroviral vectors, transposons or other DNA elements which promote integration of DNA sequences in chromosomes.

The genes coding for D-arabitol dehydrogenase and xylitol dehydrogenase (EC 1.1.1.9) under control of suitable promoters can be combined in one plasmid construction and introduced into the host cells of an D-arabitol producing organism by transformation. The nature of the plasmid vector will depend on the host organism. Thus, for Z. *rouxii* vectors incorporating the DNA of the pSR1 cryptic plasmid (Ushio, K. et al., *J. Ferment. Technol.* 66: 481–488 (1988)) are used in the preferred embodiment of the present invention. For other yeast or fungal species for which autonomously replicating plasmids are unknown, integration of the xylitol dehydrogenase (EC 1.1.1.9) and D-arabitol dehydrogenase genes into the host's chromosome can be employed. Targeting the integration to the ribosomal DNA (DNA encoding ribosomal RNA) locus of the host is the preferred method of obtaining the high copy-number integration and high level expression of the two dehydrogenase genes such targeting can be achieved by providing recombinant DNA sequences on the recombinant construct sufficient to direct integration to this locus. The genetic markers used for the transformation of the D-arabitol-producing microorganisms are preferably dominant markers conferring resistance to various antibiotics such as gentamicin or phleomycin or heavy metals, such as copper, or the like. The selectable marker gene can either be directly linked to the DNA gene sequences to be expressed, or introduced into the same cell by co-transformation.

Besides introduction of D-arabitol dehydrogenase and xylitol dehydrogenase (EC 1.1.1.9) genes. other genetic modifications can be used for constructing novel xylitol-producing strains. Thus, the genes coding for the enzymes of the oxidative pentose phosphate pathway can be overexpressed in order to increase the rate of synthesis of D-arabitol precursor D-ribulose-5-phosphate. Also, the gene coding for transketolase-the enzyme catalyzing the catabolism of pentulose-5-phosphates or pentose-5-phosphates— may be inactivated by conventional mutagenesis or gene disruption techniques leading to increased accumulation of five-carbon sugar phosphates. Inactivation of the D-xylulokinase gene can increase xylitol yield by eliminating the loss of D-xylulose due to phosphorylation. A combination of an inactivating transketolase mutation with the overexpression of D-ribulose-5-epimerase can be used for creating a different type of xylitol production pathway in which D-arabitol is not used as an intermediate.

To express a desired protein and/or its active derivatives, transcriptional and translational signals recognizable by an appropriate host are necessary. The cloned coding sequences, obtained through the methods described above, and preferably in a double-stranded form, can be operably linked to sequences controlling transcriptional expression in an expression vector, and introduced into a host cell, either prokaryote or eukaryote, to produce recombinant protein or a functional derivative thereof. Depending upon which strand of the coding sequence is operably linked to the sequences controlling transcriptional expression, it is also possible to express antisense RNA or a functional derivative thereof.

Expression of the protein in different hosts can result in different post-translational modifications which can alter the properties of the protein. Preferably, the present invention encompasses the expression of the protein or a functional derivative thereof, in eukaryotic cells, and especially in yeast.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a coding sequence and a promoter region sequence linked to the 5' end of the coding sequence) are said to be operably linked if induction of promoter function results in the transcription of mRNA encoding the desired protein and if the nature of the linkage between the two DNA sequences does not (1) alter the reading frame of a coding sequence, (2) interfere with the ability of the expression regulatory sequences to direct the expression of the protein, antisense RNA, or (3) interfere with the ability of the DNA template to be transcribed. Thus, a promoter region would be operably linked to a DNA sequence if the promoter was capable of effecting transcription of that DNA sequence.

The precise nature of the regulatory regions needed for gene expression can vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene. Such transcriptional control sequences can also include enhancer sequences or upstream activator sequences, as desired.

Expression of a protein in eukaryotic hosts such as yeast requires the use of regulatory regions functional in such hosts, and preferably yeast regulatory systems. A wide variety of transcriptional and translational regulatory sequences can be employed, depending upon the nature of the host. Preferably, these regulatory signals are associated in their native state with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from yeast genes which encode a mRNA product capable of translation are preferred, and especially, strong promoters can be employed provided they also function as promoters in the host cell. Preferred strong yeast promoters include the GAL1 gene promoter, glycolytic gene promoters such as that for phosphoglycerolkinase (PGK), or the constitutive alcohol dehydrogenase (ADC1) promoter (Ammerer, G. *Meth. Enzymol.* 101C: 192–201 (1983); Aho, *FEBS Lett.* 291: 45–49 (1991)).

As is widely known, translation of eukaryotic mRNA is initiated at the codon which encodes the first methionine. For this reason, it is preferable to ensure that the linkage between a eukaryotic promoter and a DNA sequence which encodes the desired protein, or a functional derivative thereof, does not contain any intervening codons which are capable of encoding a methionine. The presence of such codons results either in a formation of a fusion protein (if the AUG codon is in the same reading frame as the protein-coding DNA sequence) or a frame-shift mutation (if the AUG codon is not in the same reading frame as the protein-coding sequence).

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., metabolite. Translational signals are not necessary when it is desired to express antisense RNA sequences.

If desired, the non-transcribed and/or non-translated regions 3' to the sequence coding for a desired protein can be obtained by the above-described cloning methods. The 3'-non-transcribed region can be retained for its transcriptional termination regulatory sequence elements; the 3-non-translated region can be retained for its translational termination regulatory sequence elements, or for those elements which direct polyadenylation in eukaryotic cells. Where the native expression control sequences signals do not function satisfactorily in a host cell, then sequences functional in the host cell can be substituted.

The vectors of the invention can further comprise other operably linked regulatory elements such as DNA elements which confer antibiotic resistance, or origins of replication for maintenance of the vector in one or more host cells.

In another preferred embodiment, especially for *Z. rouxii*, the introduced sequence is incorporated into a plasmid vector capable of autonomous replication in the recipient host. Any of a wide variety of vectors can be employed for this purpose.

Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Preferred yeast plasmids will depend on the host. For *Z. rouxii* vectors based on the native cryptic plasmids pSR1 (Toh, E. et al., *J. Bacteriol.* 151: 1380–1390 (1982)), pSB1, pSB2, pSB3 or pSB4 (Toh, E. et al., *J. Gen. Microbiol.* 130: 252–2534 (1984)) are preferred. Plasmid pSRT303D (Jearnpipatkul, A., et al., *Mol. Gen. Genet.* 206: 88–84 (1987)) is an example of useful plasmid vector for Zygosaccharomyces yeast.

Once the vector or DNA sequence containing the construct(s) is prepared for expression, the DNA construct (s) is introduced into an appropriate host cell by any of a variety of suitable means, including transformation. After the introduction of the vector, recipient cells are grown in a selective medium, which selects for the growth of vector-containing cells. Expression of the cloned gene sequence(s) results in the production of the desired protein, or in the production of a fragment of this protein. This expression can take place in a continuous manner in the transformed cells, or in a controlled manner, for example, by induction of expression.

To construct the hosts of the invention that have been altered such that they can no longer express a certain gene product, site-directed mutagenesis can be performed using techniques known in the art, such as gene disruption (Rothstein, R. S., *Meth. Enzymol.* 101C:202–211 (1983)).

IV. Production of Xylitol

When recombinant arabitol producing yeast, preferably osmophilic, are used as hosts of the invention, they can be grown in high osmotic pressure medium, for example medium containing 10–60% D-glucose, and preferably 25% D-glucose. ("Normal" medium usually contains only 2–3% glucose.) High osmotic pressure medium induces D-arabitol formation in wild type strains of osmophilic yeasts such as *Z. rouxii*. The culture medium of the recombinant and control (wild type) strains is analyzed according to methods known in the art, at different cultivation times, for the presence of xylitol. In cultivation conditions not optimized for maximum D-arabitol yield, the experimental strain *Z. rouxii* ATCC 13356[pSRT(AX)-9] produced and secreted into the culture media both xylitol and D-arabitol. Only D-arabitol was detected in the culture medium of the control strain. The yield of xylitol in the first trials [see Table 4 in example 4] was approximately 7.7 g/l after 48 hours of cultivation.

Xylitol can be purified from the medium of the hosts of the invention according to any technique known in the art. For example, U.S. Pat. No. 5,081,026, incorporated herein by reference, described the chromatographic separation of xylitol from yeast cultures. Thus, from the fermentation step, xylitol can be purified from the culture medium using chromatographic steps as described in U.S. Pat. No. 5,081, 026, followed by crystallization.

Having now generally described the invention, the same will become better understood by reference to certain specific examples that are included herein for purposes of illustration only and are not intended to be limiting unless otherwise specified.

EXAMPLES

Example 1

Cloning of the bacterial D-arabitol dehydrogenase gene

Figure 1:
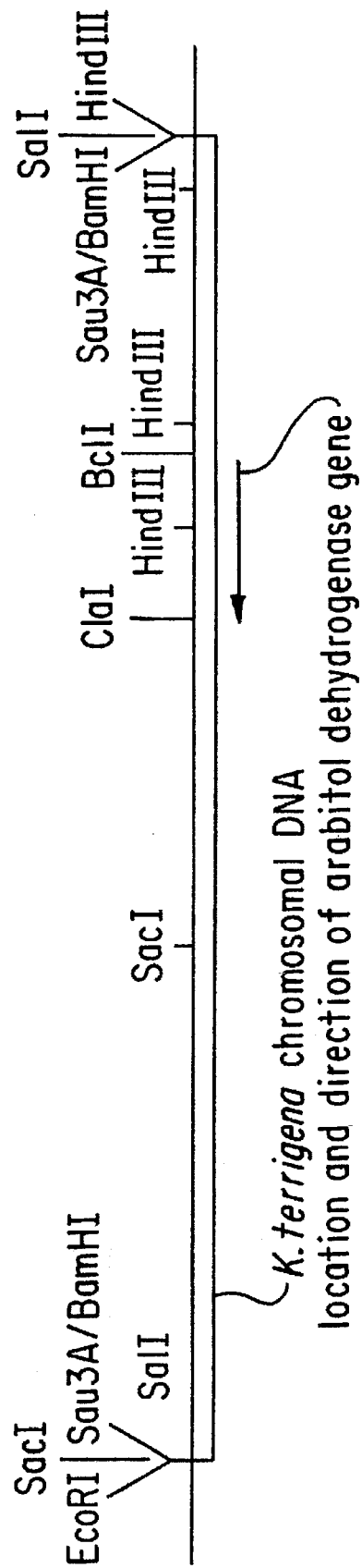
FIG. 1 is a restriction map of the insert in plasmid pARL2. This insert is that of the *Klebsiella terrigena* Php1 chromosomal locus and contains the *K. terrigena* D-arabitol dehydrogenase gene. The open box represents *K. terrigena* chromosomal DNA. The arrow shows the location and direction of the D-arabitol dehydrogenase (EC 1.1.1.11) gene in this DNA.

*Klebsiella terrigena* Php1 (obtained from K. Haahtela, Helsinki University, see Haahtela et al., *Appl. Env. Microbiol.* 45: 563–570 (1983)) was grown in 1 liter of LB medium (1% tryprone, 0.5% yeast extract, 1% NaCl) overnight at 30° C. Bacterial cells (approximately 5 g) were collected by centrifugation, washed once in TE (10 mM tris-HCl, 1 mM EDTA, pH 7.5) and resuspended in TE containing 1% sodium dodecyl sulfate and 200 µg/ml proteinase K. The suspension was incubated at 37° C. for 30 rain and then extracted once with an equal volume of phenol and two times with chloroform. 3M sodium acetate ($\frac{1}{10}$ of volume) and ethanol (3 volumes) were added and the precipitated nucleic acids collected by centrifugation and redissolved in 5 ml of TE. The RNA was removed by centrifugation of the solution through 25 ml of 1M NaCl overnight at 30,000 rpm in a Beckmann Ti50.2 rotor. The *K. terrigena* chromosomal DNA obtained by the above method had an average fragment size of more then 50,000 base pairs (bp). The DNA was then digested by the restriction endonuclease Sau3A in the supplier's (Boehringer's) buffer at an enzyme:DNA ratio of 5U/mg until the average DNA fragment size was reduced to approximately 5–10 kb (assessed by agarose gel electrophoresis). The digest was fractionated by electrophoresis through a 20×10×0.6 cm 0.6% agarose gel in TBE buffer (0.09M tris-boric acid, 1 mM EDTA, pH 8.3) at 5 V/cm overnight, a well was cut in the agarose slab at a position corresponding to a fragment size of approximately 5 kb, a piece of dialysis membrane was fixed along the well and electrophoresis was continued until essentially all the DNA fragments larger then 5 kb were adsorbed on the membrane. The plasmid DNA of pUC19 (purchased from Pharmacia) was digested with the restriction endonuclease BamHI and bacterial alkaline phosphatase using the supplier's buffer and reaction conditions. The linear form of pUC19 was purified by preparative gel electrophoresis using the membrane electroelution method described above and ligated with the 5–15 kb fraction of the *Klebsiella terrigena* chromosomal DNA. The ligation mixture was used to transform competent cells of *E. coli* SCS1 (purchased from Stratagene) to ampicillin resistance. In this experiment, approximately 10,000 recombinant clones were obtained. The pooled cells from the transformation plates were spread onto minimal medium plates containing D-arabitol (1%) as the sole carbon source. After two days of incubation at 37° C. several colonies were obtained. Plasmid DNA was isolated from two (fastest growing) of these clones and used to retransform *E. coli* strain HB101, which is unable to catabolize D-arabitol but able to use D-xylulose. All the transformants proved to be D-arabitol-utilization positive on McConkey (obtained from Difco) agar-D-arabitol plates while all control clones (the same strain transformed with pUC19) were negative. Restriction analysis has shown that the two isolated clones contained identical plasmids. One of the two isolated plasmids (named pARL2) was used for further characterization. A restriction map of the cloned 9.5 kb (approximately) fragment of *K. terrigena* DNA in pARL2 bearing the D-arabitol dehydrogenase gene is represented in FIG. 1.

Example 2

Expression of the bacterial D-arabitol dehydrogenase gene in yeast

Figure 2:
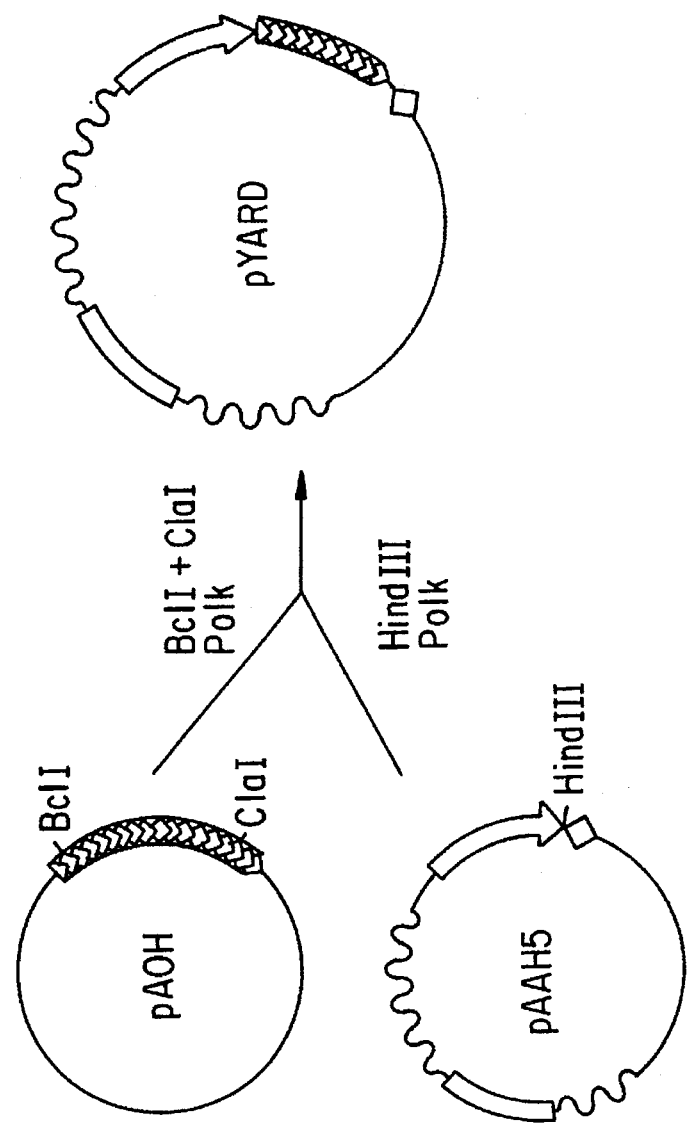
FIG. 2 shows the construction of pYARD from pADH and pAAH5. On the plasmid diagrams, the single line (−) indicates bacterial sequences; the wavy line indicates *S. cerevisiae* 2 μm DNA; the open arrow (→) indicates the ADCI promoter (the ADCI gene codes for *S. cerevisiae* alcohol dehydrogenase or ADCI, formerly called ADHI); the open diamond (◊) indicates the ADCI transcriptional terminator; the rectangular block indicates the LEU2 gene; and the hatched arrow indicates the D-arabitol dehydrogenase gene.

From the original *K. terrigena* 9.5 kb DNA clone containing the D-arabitol dehydrogenase gene an approximately 1.8 kb SacI-HindIII fragment was subcloned using conventional recombinant DNA techniques and found to contain the D-arabitol dehydrogenase gene. The plasmid containing this DNA fragment in the pUC19 vector (pADH, where ADH mean D-arabitol dehydrogenase) was isolated from *E. coli* strain JM110, digested with BclI and ClaI restriction endonucleases and a 1.38 kb DNA fragment was isolated by preparative agarose gel electrophoresis. This DNA fragment was treated with the Klenow fragment of DNA-polymerase I in the presence of all four deoxynucleotide triphosphates and ligated with a yeast expression vector pAAH5 (Ammerer, *Meth. Enzymol.* 101: 192–203 (1983)) that had been cut with HindIII and treated with Klenow fragment (FIG. 2). The resulting expression plasmid, pYARD, is a shuttle *E. coli-Saccharomyces cerevisiae* vector containing a bacterial (*E. coli*) origin of replication and ampicillin resistance gene, a yeast (*S. cerevisiae*) origin of replication from 2 μm DNA, and the yeast (*S. cerevisiae*) LEU2 gene for selection in yeast. The expression cassette includes a yeast alcohol dehydrogenase I (ADCI) promoter and (ADCI) transcription terminator flanking and operably linked to the *K. terrigena* D-arabitol dehydrogenase gene.

*Saccharomyces cerevisiae* strain GRF18 (MATα, leu2-3, 112, his3-11,15) and *S. cerevisiae* strain DBY746 (ATCC 44773; MATα, leu2-3,112 his3-A1 urn3-52 trp1-289) were both used as the hosts for transformation with D-arabitol dehydrogenase expression vector pYARD described above, with the same results. The transformation was performed by the standard lithium chloride procedure (Ito et al., *Bacteriol.* 153: 163–160 (1983)) using the LEU2 marker of pYARD for transformant selection. The transformants were grown in liquid culture in minimal medium: 0.67% yeast nitrogen base ("Difco"), 2% D-glucose, 100 mg/l of histidine and tryptophane at 30° C. overnight with shaking. Cells were collected by centrifugation, suspended in a minimal volume of 0.1M potassium phosphate buffer pH 6.8, containing 1 mM $NAD^+$ and disrupted with 0.5 mm glass beads in a Bead beater apparatus ("Biospec products") for 6 minutes with ice cooling. D-arabitol dehydrogenase activity was measured as described above. An D-arabitol-grown *K. terrigena* cell extract was used as a positive control in these experiments and DBY746 transformed with pAAH5 as negative control. The results presented in Table 1 show that D-arabitol dehydrogenase gene isolated from *K. terrigena* is expressed efficiently in yeast.

TABLE 1

| Microbial strain | D-arabitol dehydrogenase activity (arbitrary units) |
| --- | --- |
| *K. terrigena* Phpl | 3.5 |
| DBY746 [pYARD] | 1.0 |
| DBY746 [pAAH5] | 0.00 |

Example 3

Construction of yeast vectors for overexpression of xylitol dehydrogenase and D-arabitol dehydrogenase genes The known nucleotide sequence of a yeast (*Pichia stipitis*) gene, XYL2, encoding xylitol dehydrogenase (Kötter et at., *Curr. Genet.* 18: 493–500 (1990)) was used to synthesize oligonucleotides for the cloning of this gene by the polymerase chain reaction. The two oligonucleotides: CGAAT-TCTAGACCACCCTAAGTCGTCCC (5'-oligonucleotide) [SEQ ID No.: 1:] and TTCAAGAATTCAAGAAACT-CACGTGATGC (3'-oligonucleotide) [SEQ ID No. :2:] were designed to incorporate convenient restriction sites XbaI and EcoRI at the 5'- and 3'-termini of the PCR product. The 5'-oligonucleotide anneals at position 1–24 of XYL2 and the 3'-nucleotide anneals at position 1531–1560, according to the numbering used in Kötter et at., *Curr. Genet.* 18: 493–500 (1990).

*Pichia slipitis* CBS6054 (Centraalbureau voor Schimmeicultures, Oosterstraat 1, PO Box 273, 3740 AG Baarn, The Netherlands) was grown overnight in YEPD medium (1% yeast extract, 2% peptone, 2% D-glucose), the cells were collected by centrifugation, washed once with 1M sorbitol solution containing 1 mM EDTA, pH 7.5, resuspended in the same solution and digested with Lyticase (Sigma). The digestion was controlled by monitoring the optical density at 600 nm of a 1:100 dilution of the cell suspension in 1% SDS. The digestion was terminated when this value dropped to approximately one seventh of the original. The spheroplast suspension was then washed four times with 1M sorbitol solution. The spheroplasts were lysed in 1% SDS and treated with 200 μg/ml proteinase K at 37° C. for 30 min. After one phenol and two chloroform extractions, the nucleic acids were ethanol precipitated and redissolved in a small volume of TE buffer. The integrity of the chromosomal DNA was checked by agarose gel electrophoresis. The average DNA fragment size was higher then 50 kb. PCR was performed using Taq DNA polymerase (Boehringer) in the supplier's buffer. The thermal cycle was 93° C.—30 sec, 55° C.—30 sec, 72° C.—60 sec. The PCR product was chloroform extracted, ethanol precipitated and digested with EcoRI and XbaI under standard conditions. After agarose gel purification, the DNA fragment was cloned into XbaI and EcoRI cut pUC18 (plasmid pUC(XYL2)). Subsequent restriction analysis confirmed that the restriction map of the cloned fragment corresponds to the nucleotide sequence of *P. stipitis* XYL2 gene.

Yeast plasmids for overexpressing D-arabitol dehydrogenase and xylitol dehydrogenase were constructed as illustrated by FIG. 3 and FIG. 4. To change the flanking restriction sites of the D-arabitol dehydrogenase expression cassette of plasmid pYARD, the whole cassette was excised by BamHI digestion and cloned into the BamHI cleaved pUC18. The resulting plasmid pUC(YARD) was digested with SalI and EcoRI and the sole 2.0 kb DNA fragment was isolated by preparative gel electrophoresis. This fragment was ligated with a 1.6 kb HindIII-EcoRI DNA fragment isolated from the plasmid pUC(XYL2) and the 6.6 kb fragment or *E. coli* yeast shuttle vector pJDB207 (Beggs, J. D. *Nature* 275: 104–109 (1978)) digested with HindIII and SalI. Plasmid pJDB(AX)-16 was isolated after transformation of *E. coli* with the above ligation mixture. This plasmid is capable of replicating in both *E. coli* and *Saccharomyces cerevisiae*. In *S. cerevisiae* it directs the high level synthesis of both D-arabitol dehydrogenase and xylitol dehydrogenase. Plasmid pSRT(AX)-9 was synthesized by ligation of the 4.7 kb SalI fragment from the plasmid pJDB(AX)-9 and the linear form of the plasmid pSRT303D (Jearnpipatkul et al., *Mol. Gen. Genet.* 206: 88–94 (1987)) obtained by partial hydrolysis with SalI.

Example 4

Construction of yeast strains secreting xylitol

*Zygosaccharomyces rouxii* ATCC 13356 was transformed with the plasmid pSRT(AX)-9 by a slight variation of a previously described method (Ushio, K. et al., *J. Ferment. Technol.* 66: 481–488 (1988)). Briefly, *Z. rouxii* cells were grown overnight in YEPD medium (giving a culture with optical density at 600 nm of 3-5), collected by low-speed centrifugation, washed twice in 1M sorbitol, 1 mM EDTA solution pH 7.5, resuspended in ⅕ of the original culture volume of the same solution containing 1% 2-mercaptoethanol and digested at room temperature with lyticase (Sigma). The digestion was followed by diluting a suitable aliquot of the cell suspension into 1% SDS solution and measuring the optical density of the diluted sample at 600 nm. When this value dropped to ⅐ of the original, the digestion was terminated by cooling the suspension on ice and washing (by a 10 min, 1000 rpm centrifugation at 0° C.) with the sorbitol solution until the mercaptoethanol smell could no longer be detected. The spheroplasts were washed once with cold 0.3M calcium chloride solution in 1M sorbitol and resuspended in the same solution in about ¼ of original culture volume. 200 µl aliquots of this suspension and 10–20 µg of plasmid DNA were mixed and incubated at 0° C. for 40 min. 0.8 ml of ice-cold 50 % PEG-6000 solution containing 0.3M calcium chloride was added to the spheroplast suspension and incubation in the cold was continued for 1 h. The spheroplasts were concentrated by centrifugation at 4000 rpm for 10 min in a table-top centrifuge, resuspended in 2 ml of YEPD containing 1M sorbitol and left for regeneration overnight at room temperature. The regenerated cells were plated onto YEPD plates containing 50–100 µg/ml of gentamicin and incubated at 30° C for 4–6 days.

The transformants were grown in liquid YEPD medium, cell extracts prepared as described for *S. cerevisiae* (Example 2), and the activities of D-arabitol dehydrogenase and xylitol dehydrogenase measured. The results of these measurements are compared with similar measurements made in other organisms in Table 2. They show that both genes are expressed efficiently in *Z. rouxii*.

The cells of *Z. rouxii* ATCC 13356 transformed with pSRT(AX)-9 were grown for two days in 50 ml of YEPD containing 50 µg/ml of gentamicin, collected by centrifugation and used to inoculate 100 ml of YEPD containing 25 wt % D-glucose and 50 µg/ml of gentamicin. This culture was grown in a 1000 ml flask on a rotary shaker (200 rpm) at 30° C. In another experiment (Experiment 2) the same medium without yeast extract (low phosphate medium) was used. Xylitol content in the culture broth was analyzed by standard HPLC and gas chromatography. The results are presented in Table 3. No xylitol was detected in the culture medium of untransformed *Z. rouxii* grown in the same media (without gentamicin).

TABLE 2

Activities of D-arabitol dehydrogenase and xylitol dehydrogenase in different organisms and strains

| Organism and strain | Plasmid(*) | D-arabitol dehydrogenase (IU/mg protein) | xylitol dehydrogenase (IU/mg protein) |
|---|---|---|---|
| *Klebsiella terrigena* Phpl | None | 0.48 | ND.(**) |
| *S. cerevisiae* DBY746 | None | 0.00 | <0.01 |
| *S. cerevisiae* DBY746 | pJDB(YARD) | 3.0 | <0.01 |
| *S. cerevisiae* DBY746 | pJDB(AX)-16 | 1.9 | 1.2 |
| *Z. rouxii* ATCC 13356 | None | 0.00 | <0.02 |
| *Z. rouxii* ATCC 13356 | pSRT(AX)-9 | 1.3 | 0.7 |

(*)The plasmids are designed to express the following enzymes:
pJDB(YARD) - D-arabitol dehydrogenase
pJDB(AX)-16 - D-arabitol dehydrogenase and xylitol dehydrogenase
pSRT(AX)-9 - D-arabitol dehydrogenase and xylitol dehydrogenase
(**)ND - Not determined

TABLE 3

Production of xylitol by the *Z. rouxii* ATCC 13356 carrying the plasmid pSRT(AX)-9 (g/l)

| Cultivation time (h) | Experiment 1 Medium with Yeast Extract | Experiment 2 Medium without Yeast Extract |
|---|---|---|
| 0 | 0.0 | 0.0 |
| 48 | 7.7 | 0.5 |
| 144 | 7.5 | 6.1 |

Using a similar approach, strains producing xylitol from other carbon sources can be constructed. For example, *Candida tropicalis* is capable of converting n-alkanes into D-arabitol (Hattori, K. and Suzuki T., *Agric. Biol. Chem.* 38: 1875–1881 (1974)) in good yield. The 4.7 kb SalI fragment from the plasmid pJDB(AX)-9 can be inserted into the plasmid pCU1 (Haas, L. et al., *J. Bacteriol.* 172: 4571–4577 (1990)) and used to transform *C. tropicalis* strain SU-2 (ura3). Alternatively, the same expression cassette can be transformed into a prototrophic *C. tropicalis* strain on a plasmid vector bearing a dominant selective marker.

Example 5

Construction of an integrative dominant selection vector for the expression of arabitol dehydrogenase and xylitol dehydrogenase and transformation of *Torulopsis candida*

Chromosomal DNA was isolated from *T. candida* (ATCC 20214) by a procedure similar to the standard procedure used for *S. cerevisiae*. However, preparation of *T. candida* spheroplasts required a high concentration of Lyticase (Sigma)—approx. 50,000 U per 10 g of cells and long incubation time—from several hours to overnight incubation at room temperature to achieve efficient cell wall lysis. The buffer for spheroplast preparartion was 1 mM EDTA, pH 8, containing 1M sorbitol and 1% mercaptoethanol. The spheroplasts were washed three times with the same buffer (without mercaptoethanol) and lysed in 15 ml of 1% SDS. Two phenol extractions were performed immediately after cell lysis and the DNA was precipitated by addition of 2 volumes of ethanol and centrifugation (5 min at 10,000 rpm). The DNA was washed twice with 70 % ethanol and dried under vacuum. The DNA was dissolved in 5 ml of 10 mM tris-HCl buffer containing 1 mM EDTA, RNAse A was added to 10 µg/ml concentration and the solution was incubated for 1 h at 37° C. The integrity of the DNA was confirmed by agarose gel electrophoresis using uncut lambda DNA as a molecular weight reference.

200 µg of the chromosomal DNA of *T. candida* was cut with HindIII and EcoRI, the digest was applied into a 6 cm wide well on an 0.7% (8×15×0.8 cm) preparative agarose gel and separated by electrophoresis. A 1 cm wide strip of the gel was cut out of the gel and blotted onto a positively charged nylon membrane (Boehringer 1209 299). The blot was probed with a 10kb DNA fragment of *Zygosaccharomyces bailii* rDNA excised with SalI from the plasmid pAT68 (K. Sugihara et al., *Agric. Biol. Chem.* 50(6): 1503–151 (1986)). The probe was labeled and the blots were developed using DIG DNA Labeling and Detection Kit (Boehringer 1093 657) according to the manufacturer's instructions. Three hybridization bands were observed corresponding to DNA fragments of approximtely 4.5, 2.7 and 1.1 kb. Using the blot as a reference, a band corresponding to the largest (4.5 kb) hybridizing DNA fragment was cut out of the remaining portion of the preparative gel, the DNA was electroeluted and ligated with pUC19 cut by EcoRI and HindIII.

The ligation mixture was used to transform *E. coli*. The transformed bacteria were plated onto a charged nylon membrane (Bio-Rad 162-0164) laying on the agar surface of a plate containing LB medium with ampicillin. After 24 h incubation at 37° C., the membrane was lifted and in situ lysis of bacterial colonies was performed according to the manufacturer's instructions. No replica plates were needed since *E. coli* penetrates this type of membrane and after the filter is lifted there is a visible trace of every bacterial colony on the agar surface. The membrane was probed with the same *Z. bailii* rDNA fragment using the same DIG detection kit as above. A number of positive clones were identified (approximately 2–5% of all clones). A restriction analysis of the plasmid mini-preparations from 8 hybridization-positive clones and 4 hybridization-negative clones was performed using a mixture of EcoRI, HindIII and EcoRV. All hybridization-positive clones produced identical restriction fragment patterns (with characteristic fragments of 0.55 and 1.5 kb) while the same patterns of the hybridization-negative clones were all different. The plasmid DNA from one of hybridization-positive clones was isolated on preparative scale and name pTCrDNA. It was concluded that the cloned piece was a fragment of *T. candida* rDNA because 1) it hybridized strongly with rDNA of *Z. bailii* and 2) it was cloned from the partially enriched *T. candida* chromosomal DNA digest with high frequency (rDNA is known to be represented by about 100 copies in yeast). A partial restriction map of the cloned DNA fragment is shown in FIG. 5.

A plasmid combining the rDNA fragment of *T. candida* with a dominant selection marker was constructed as follows. Plasmid pUT332 (Gatignol, A., et al., *Gene* 91: 35–41 (1990)) was cut with HindIII and KpnI, the 1.3 kb DNA fragment was isolated by agarose electrophoresis, and ligated with the 4.5 kb HindIII-EcoRI fragment from pTCrDNA and pUC19 digested with EcoRI and KpnI (FIG. 6). The ligation mixture was transformed into *E. coli* and a clone bearing the plasmid pTC(PHLE) was identified by restriction analysis.

PTC(PHLE) was partially digested with SalI and the linear form of the plasmid was purified by agarose gel electrophoresis. It was ligated with a 5 kb SalI fragment isolated from pJDB(AX)-16 (Example 2). Plasmid pTC (AX) was identified among the clones obtained after transformation of this ligation mixture into *E. coli* (FIG. 6). This plasmid contains the following functional elements:

a) bacterial phleomycin-resistance gene under control of a yeast promoter and transcription terminator enabling the direct selection of the yeast cells transformed by this plasmid;

b) a piece of *T. candida* rDNA providing a target for homologous recombination with *T. candida* chromosome and improving the efficiency of transformation;

c) the expression cassette for arabitol-dehydrogenase and xylitol dehydrogenase genes providing for the syntheseis of the two enzymes of arabitol-xylitol conversion pathway.

Example 6

Transformation of *T. candida* and analysis of xylitol production

The plasmid pTC(AX) was used to transform the *Torulopsis candida* strain ATCC 20214. *T. candida* was grown for 36 h in YEPD medium containing 10% glucose. The cells were collected by centrifugation (2000 rpm for 10 min at 4° C.) and washed three times with sterile 1M sorbitol. The cell pellet was suspended in an equal volume of cold 1M sorbitol, 200 µl aliquotes were mixed with pUT(AX) DNA (20–100 µg) and then transferred into ice-cold 2 mm electrode gap electroporation cuvettes and electroporated using Invitrogen ElectroPorator apparatus with the following settings: voltage 1800 V, capacitance 50 µF, parallel resistance 150 Ω. The cells were transferred into 2 ml of YEPD containing 1M sorbitol and incubated ovenight at 30° C. on a shaker. The transformed cells were collected by low speed centrifugation, and plated onto plates containing YEPD medium titrated to pH 7.5 and containing 30 µg/ml of phleomycin. The plates were incubated at 30° C. for 7–10 days. Most of the yeast colonies that developed during this time were background routants since similar number of colonies appeared also on the control plates (which contain cells treated similarly but without addition of DNA). To distinguish true transformants from spontaneous mutants, the chromosomal DNA was isolated from 72 individual yeast colonies by a scaled down procedure for isolating *T. candida* chromosomal DNA described above. 10 µg of each of these DNA preparations was cut with a mixture of EcoRI and BamHI. The digests were separated on a 1% agarose gels and then blotted onto a positively charged nylon membrane as described in Example 5. The blots were probed with DNA from the plasmid pADH (Example 2) which contains arabitol-dehydrogenase sequences and pUC sequences but no DNA fragments of yeast origin (to avoid hybridization between possible homologous yeast sequences). The probe was labeled and the blots were developed using DIG DNA Labeling and Detection Kit (Boehringer 1093 657). Only one clone (*T. candida*::pTC(AX)) with a hybridization signal compatible with the structure of the transforming plasmid (three bands in the 2–3 kb region) was discovered indicating a very low transformation efficiency. A positive hybridization signal was detected for one more clone, however, the position of the only hybridizing band (about 5–7 kb) indicated that either only a fragment of the pTC (AX) has integrated into yeast chromosome or some rearrangement occurred at the integration site. We assumed that the plasmid had integrated into the *T. candida* chromosome. This assumption is compatible with the observation that after growth in non-selective medium and cloning, all clones of *T. candida*::pTC(AX) retain the phleomycin resistant phenotype.

The *T. candida*::pTC(AX) transformant was grown in YEPD medium containing 10% glucose for 36 h, and the arbitol dehydrogenase and xylitol dehydrogenase activities were measured as described in Example 4. The results are presented in Table 4.

TABLE 4

Arabitol dehydrogenase and xylitol dehydrogenase activities in wild type *T. candida* and the strain transformed with pTC(AX). (IU/mg protein)

| *T. candida* | Arabitol dehydrogenase | Xylitol dehydrogenase |
| --- | --- | --- |
| Wild type | 0.02 | 0.03 |
| Transformant | 0.03 | 0.05 |

The activity of xylitol-dehydrogenase was not significantly increased over the activity level of endogenous *T. candida* xylitol dehydrogenase. The activity of plasmid-encoded arabitol-dehydrogenase (EC 1.1.1.11) was difficult to separate from the activity of endogeneous synonymous but different (ribulose-forming, EC 1.1.1.) arabitol dehydrogenase. The only definitive conclusion from this experiment was that the expression level of both enzymes was much lower than in *Z. rouxii*. Attempts to increase the plasmid copy number and the expression level of the two dehydrogenases of the integrated plasmid by cultivating *T. candida*::pTC(AX) on media with increasing concentrations of phleomycin were not successful.

The xylitol production by the *T. candida*::pTC(AX) was tested after growing it on YEPD containing 10% glucose for 5–7 days. In three separate experiments, the transformant produced 1.1; 1.6; and 0.9 g/l xylitol, while no xylitol was detected in the culture medium of the wild type *T. candida* by HPLC. The detection limit of the analytical method we employed is lower then 0.1 g/1. Therefore, it is possible to conclude that xylitol production by *T. candida*::pTC(AX) is in fact determined by the plasmid.

Example 7

Transformation of Candida polymorpha with arabitol-dehydrogenase and xylitol-dehydrogenase genes.

In order to introduce arabitol dehydrogenase and xylitol-dehydrogenase genes into *Candida polymorpha*, a mutant in the orotidine phosphate decarboxylase gene (hereinafter called also URA3) was isolated using a modification of the method of Boeke et al. (Boeke, J. D., et al., *Mol. Gen. Genet.* 197: 345–346 (1984)). *C. polymorpha* strain ATCC 20213 was grown for 24 h in YEPD, the cells were collected by centrifugation (2000 rpm, 10 min), washed with water two times and suspended in three volumes of sterile 0.1M sodium phosphate buffer pH 7.0. Ethyl methanesulfonate was added to 1% concentration and the cells were incubated for 2h at room temperature. The reaction was stopped by transferring the cells into 0.1M sodium thiosulfate solution and washing them three times with sterile water. Mutagenized cells were transferred into 0.5 liters of YEPD and grown at 30° C. with shaking for two days. The yeast was collected by centrifugation, washed two times with water and transferred into 1 liter of medium containing 0.7% Yeast Nitrogen Base (Difco), 2% glucose (SC medium) and incubated on a rotary shaker for 24 h at 30° C. 1 mg of nystatin was added to the culture and the incubation continued for 4 hours. Nystatin-treated cells were separated from the medium by centrifugation, washed two times with water, and transferred into 1 liter of SC medium containing 50 mg/liter of uracil. The cells were incubated on a rotary shaker for 5 days and then plated on SC medium plates containing 50 mg/liter uracil and 1 g/liter of fluoroorotic acid. After incubating the plates for two weeks at 30° C., approximately 400 fluoroorotic acid reistant colonies were obtained and all of them were tested for uracil auxotrophy. Five uracil-dependent clones were isolated. However, three clones did grow on uracil-free medium, although at a reduced rate. Two clones (named *C. polymorpha* U-2 and *C. polymorpha* U-5) which had a clear uracil-dependent phenotype were used for transformation experiments.

Cloning of the *C. polymorpha* URA3 gene was achieved by a conventional strategy. The chromosomal DNA was isolated by the method described in Example 5. The DNA was partially cut with Sau3A and fractionated on agarose gels. Several fractions were collected and their molecular size distribution was checked by analytical gel electrophoresis. The fractions in the range of 5 to 10 kb were used for cloning experiments. The vector used for construction of the library, pYEp13 (Broach et al., *Gene* 8: 121–133 (1979)), contains the *S. cerevisiae* LEU2 gene, 2μ origin of replication and a unique restriction site for BamHI. The vector was cut with BamHI, purified by agarose gel electrophoresis and dephosphorylated with bacterial alkaline phosphatase. Several independent vector preparations and ligation conditions varying the vector to insert ratio and reaction volume) were tested in small scale experiments to optimize for the largest number of transformants and highest percentage of recombinant clones (analysed by restriction analysis of plasmid minipreps from random clones). The large scale ligations were performed using the optimized conditions and transformed into *E. coli* strain XL1-BLUE. The constructed library included about 15,000 primary transformants approximately 90% of which were insert-containing.

Yeast strain DBY746 (MATalpha, leu2-3, 112, his3-A 1, trp 1-289, ura3-52) was transformed with a *C. polymorpha* gene library. Each library pool was transformed into *S. cerevisiae* separately using about 20 μg of plasmid DNA and plating the transformation on one plate supplemented with uracil, tryptophan and histidine (i.e. using only leucine selection). 3,000–10,000 yeast transformants per plate were obtained. The yeast transformants were then replica plated on plates with mininal medium supplemented with tryptophan and histidine (uracil minus plates). Control replicas on histidine-histidine (uracil minus plates). Control replicas on histidine-minus and tryptophan-minus plates were also made. One to four uracil-independent clones appeared on almost every plate. The histidine-independent and tryptophan-independent isolates were also obtained, however the number of isolates was 2–3 times lower then for URA3 isolates.

Plasmids from six of the uracil-independent clones were rescued into *E. coli*, isolated on a preparative scale and used to re-transform DBY746 to leucine prototrophy. 10–20 random colonies from each transformation were then checked for uracil dependence. Five out of six rescued plasmids transformed DBY746 to the Leu⁺ Ura⁺ phenotype. Restriction analysis of the five plasmids named revealed very similar restriction patterns. Those patterns were too complex to produce an unambiguous restriction map of the cloned fragment. However, it was found that HindIII digestion generates in all clones a fragment covering most of the DNA insert (approximately 4.5 kb). This fragment from one of the C. polymorpha URA3 isolates—pCP291—was purified by agarose gel electrophoresis and subcloned into pJDB(AX) partially digested with HindIII. The structure of the plasmid pCPU(AX) isolated as a result of this cloning experiment is shown in FIG. 7A.

Transformation of both C. polymorpha U-2 and C. polymorpha U-5 was attempted using the same electroporation conditions as described in Example 6. The electroporated cells, after overnight shaking in YEPD containing 1M sorbitol, Zwere plated on SC medium plates. After 10 days of incubation at 30° C., approximately 100 colonies were observed on the plate containing C. polymorpha U-2 transformed with pCPU(AX), while the number of colonies on the control plate (containing similarly treated cells of this strain without added DNA) was only 14. C. polymorpha U-5 failed to demonstrate a signficant effect in a transformation experiment over the no-DNA-control. Three random clones from the C. polymorpha U-2 transformation plate were first streaked on a fresh SC medium plate and these streaks used to inoculate 100 ml cultures of YEPD containing 15% glucose. The control culture was inoculated with C. polymorpha U-2. After incubation on a rotary shaker (200 rpm) at 30° C. for 10 days, the xylitol content in the culture medium was analysed by HPLC. The results of this experiment are presented in Table 5.

TABLE 5

Xylitol production by C. polymorpha U-2 transformed with pCPU(AX)

| Strain | Xylitol (mg/ml) |
| --- | --- |
| C. polymorpha U-2 | 0.0 |
| C. polymorpha U-2::pCPU(AX)-1 | 0.5 |
| C. polymorpha U-2::pCPU(AX)-2 | 0.0 |
| C. polymorpha U-2::pCPU(AX)-3 | 2.1 |

Considerable variation in the level of xylitol production between different clones was observed. It may be a consequence of integration of the pasmid pCPU(AX) at different loci of the C. polymorpha chromosome. Strain C. polymorpha U-2::pCPU(AX)-2 is probably a revertant and not a true transformant. However, these experiments clearly demonstrated that the arabitol-xylitol pathway may also be introduced into C. polymorpha.

Example 8

Cloning of the enzymes of oxidative pentose phosphate pathway and their overexpression in osmophilic yeast The first enzyme of the oxidative pentose phosphate pathway—D-glucose-6-phosphate dehydrogenase is coded in S. cerevisiae by the ZWF1 gene. The sequence of this gene is known (Nogae T., and Johnston, M. Gene 96: 161–19 (1990); Thomas D. et al., The EMBO J. 10: 547–553 (1991)). The gene including the complete coding region, 600 bp of the 5'-noncoding region and 450 bp of the 3'-noncoding region has been cloned by PCR using the two oligonucleotides: CAGGCCGTCGACAAG-GATCTCGTCTC (5'-oligonucleotide) [SEQ ID No. :3:] and AATTAGTCGACCGTTAATTGGGGCCACTGAGGC (3'-oligonucleotide) [SEQ ID No.:4:]. The 5'-oligonucleotide anneals at positions 982–1007 and the 3'-oligonucleotide anneals at position 3523–555 in the numbering of D-glucose-6-phosphate dehydrogenase as described in Nogae T., and Johnston, M. Gene 96: 161–19 (1990). The chromosomal DNA was isolated from S. cerevisiae strain GRF18 by the method described in Example 3. The PCR parameters were the same as in Example 3. The amplified DNA fragment containing the ZWF1 gene was digested with SalI and cloned into pUC19 digested with the same restrictase resulting in plasmid pUC(ZWF). The identity of the cloned gene was checked by restriction analysis.

The second enzyme of the pentose phosphate pathway, 6-phosphogluconic acid dehydrogenase is coded in E. coli by the gnd gene. The nucleotide sequence of this gene is known (Nasoff, M. S. et al., Gene 27: 253–264 (1984)). In order to clone the gnd gene from E. coli, the chromosomal DNA was isolated from the E. coil strain HB101 by a method identical to the method used for isolation of the Klebsiella terrigena DNA (Example 1 ). The oligonucleotides (GCGAAGCTTAAAAATGTCCAAGCAACAGA-TCGGCG [SEQ ID No. :5:] and GCGAAGCTTAGAT-TAATCCAGCCATTCGGTATGG [SEQ ID No.:6:]) for the PCR amplification of the gnd gene were designed to amplify only the coding region and to introduce HindIII sites immediately upstream of the initiation codon and immediately downstream of the stop codon. The 5'-oligonucleotide anneals at positions 56–78 and the 3'-oligonucleotide anneals at position 1442–1468 in the numbering of 6-phosphogluconic acid dehydrogenase as described in Nasoff, M .S . et al., Gene 27: 253–264 (1984). The amplified DNA fragment was digested with HindIII and ligated with the HindIII digested vector pUC19. Ten independent apparently identical clones of the resulting plasmid pUC(gnd) were pooled. This was done in order to avoid possible problems associated with the sequence errors which might be introduced during PCR amplification. The coding region of the gnd gene was fused with the S. cerevisiae ADCI promoter and transcription terminator by transferring the 1.4 kb HindIII fragment from the pUC(gnd) pool into the expression vector pAAH5 (Ammerer, Meth. Enzymol. 101: 192–203 (1983)). Several independent clones of the resulting plasmid pAAH(gnd) were transformed into S. cerevisiae strain GRF18 by the lithium chloride procedure (Ito et al., J. Bacteriol. 153: 163–168 (1983)) and the activity of 6-phospho-D-gluconate dehydrogenase was measured in the transformants. In all the transformants, the activity of the 6-phospho-D-gluconate dehydrogenase was elevated several times relative to the untransformed host indicating that the bacterial 6-phospho-D-gluconate dehydrogenase can be efficiently expressed in yeast. The clone of pAAH(gnd) which produced the highest activity in yeast was chosen for further constructions. The cloning of the ZWF1 and gnd genes as well as the construction of the pAAH(gnd) plasmid are illustrated by FIG. 8 and 8a.

In order to overexpress simultaneously both D-glucose-6-phosphate dehydrogenase and 6-phospho-D-gluconate dehydrogenase genes in an osmophilic yeast host, the plasmid pSRT(ZG) was constructed. The method for constructing this plasmid is illustrated by FIG. 9. Briefly, the 6-phospho-D-gluconate dehydrogenase expression cassette from the plasmid pAAH(gnd) was transferred as a 3.1 kb BamHI DNA fragment into BamHI cut pUC19. The resulting plasmid pUC(ADHgnd) was cleaved with SacI and XbaI and a 3.1 kb DNA fragment was purified by agarose gel electrophoresis. This fragment was simultaneously ligated with two other DNA fragments: 2.5 kb fragment of the pUC(ZWF) obtained by digestion with SacI and partial digestion with PstI and a vector fragment of the plasmid pSRT(AX)-9 (Example 3) digested with PstI and XbaI. The structure of the resulting plasmid pSRT(ZG) was confirmed by restriction analysis. After transforming Z. rouxii ATCC 13356 with pSRT(ZG) (by the method described in Example 4) the activity of D-glucose-6-phosphate dehydrogenase and 6-phospho-D-gluconate dehydrogenase was measured in the transformed strain. Both enzymes had approximately twenty times higher activities in the transformed strain than in the untransformed control (Table 6). Similar methods can be used to achieve overexpression of the two genes coding for enzymes of the oxidative part of the pentose phosphate pathway in other yeast species. However, since there are no vectors capable of being maintained as extrachromosomal plasmids in most yeast species other than Saccharomyces or Zygosaccharomyces—integrative transformation is the only useful method for such hosts. The preferred type of integrative vectors are the vectors targeted for integration at the ribosomal DNA locus since vectors of this type provide for high copy number integration and consequently for higher expression level (Lopes, T. S. et al., Gene 79: 199–206 1989)).

TABLE 6

Activity of the D-glucose-6-phosphate dehydrogenase and 6-phospho-D-gluconate dehydrogenase in Z. rouxii ATCC 13356 transformed with pSRT(ZG) and untransformed control (μmole/min*mg of protein)

| Yeast strain | D-glucose-6-P dehydrogenase | 6-P-Gluconate dehydrogenase |
| --- | --- | --- |
| Z. rouxii (untransformed) | 0.33 | 0.45 |
| Z. rouxii [pSRT(ZG)] | 7.3 | 7.7 |

Example 9

Construction of the transketolase routants in yeast

The transketolase mutants in yeast can be obtained most conveniently by a site directed gene disruption method although conventional methods of chemical mutagenesis are also applicable. A homologous transketolase gene cloned from the yeast species in which the mutation is desired will generally be necessary to apply the gene disruption technology although sometimes a heterologous clone from a very closely related species can also be used. The sequence of the transketolase gene from S. cerevisiae is known (Fletcher, T. S., and Kwee, I. L., EMBL DNA sequence library, ID:SCTRANSK, accession number M63302). Using this sequence, the S. cerevisiae transketolase gene was cloned by PCR. Oligonucleotides AGCTCTAGAAAT-GACTCAATTCACTGACATTGATAAGCTAGCCG [SEQ. ID No.:7:] and GGAGAATTCAGCTTGTCACCCTTATA-GAATGCAATGGTCTTTTG [SEQ ID No.:8:] and the chromosomal DNA from S. cerevisiae (isolated as described above) were used for the amplification of the DNA fragment containing the transketolase gene. The 5'-oligonucleotide anneals at positions 269–304 and the 3'-oligonucleotide anneals at position 2271–2305 in the numbering of transketolase as described in (Fletcher, T. S., and Kwee, I. L., EMBL DNA sequence library, ID:SCTRANSK, accession number M63302). The fragment was digested with XbaI and EcoRI and cloned into the pUC19 cleaved with the same enzymes. The restriction analysis of the resulting plasmid pUC(TKT) confirmed the identity of the cloned DNA fragment. This plasmid was cut with BglII and ClaI and the large DNA fragment was purified by agarose electrophoresis. This fragment was ligated with two DNA fragments isolated from the plasmid pUT332 (Gatignol, A. et al., Gene 91: 35–41 (1990)): a ClaI-PstI fragment bearing the URA3 gene and the 3'-part of the bleomycin resistance gene and a BamHI-PstI DNA fragment bearing the yeast TEF1 (transcription elongation factor 1) promoter and the 5'-part of the bleomycin resistance gene coding sequence. After transformation of E. coli with the above ligation mixture and restriction analysis of the plasmid clones, the plasmid pTKT(BLURA) was isolated. This plasmid contains the coding sequence of S. cerevisiae transketolase gene in which the 90 bp fragment of between the ClaI and BglII sites is substituted with a fragment of pUT332 containing two markers selectable in S. cerevisiae—the URA3 gene and the bleomycin resistance gene under control of the TEF1 promoter and CYC1 transcription terminator. The plasmid was used to transform S. cerevisiae strain DBY746 (ATCC 44773; MATα his3A1 leu2-3, 112 ura3-52 trp1-289) to phleomycin resistance (10 μg/ml phleomycin in YEPD medium) by the lithium chloride method (Ito et al., J. Bacteriol. 153: 163–168 (1983)). The transformants were tested for uracil prototrophy and for the ability to grow on D-xylulose. Five URA3 clones, three of which displayed reduced growth on D-xylulose, were grown in 100 ml cultures, cell extracts were prepared by shaking with glass beads and the transketolase activity was measured in the crude extracts. The assay was performed in 0.1M glycyl-glycine buffer pH 7.6 containing 3 mM magnesium chloride, 0.1 mM thiamine pyrophosphate, 0.25 mM NADH, and 0.2 mg/ml bovine serum albumin. Immediately before measurement 3 μl of a solution containing 0.5M D-xylulose-5-phosphate and 0.5M ribose-5-phosphate were added to 1 ml of the above buffer followed by 7.5 U of triose phosphate isomerase and 1.5 U of α-glycerophosphate dehydrogenase (both from Sigma). The reaction was initiated by adding a suitable aliquot of the crude extract and followed by recording the decrease of optical density at 340 nm. The cellular extract of the strain DBY746 was used as a control. The transketolase activity in the crude extract of DBY746 and the two transformants with unretarded growth on D-xylulose was readily measurable at approximately 0.25 U/mg protein. The three transformants with reduced growth on D-xylulose had transketolase activity below the detection limit of our method (at least 20 times lower than wild-type). The activities of D-glucose-6-phosphate dehydrogenase and 6-phospho-D-gluconate dehydrogenase were also measured as a control for possible enzyme inactivation during the preparation of the cell extracts. The activities of these two enzymes were very similar in all six strains. Therefore, it was concluded that the three clones which grew poorly on D-xylulose contained the mutation in the transketolase gene. The growth of the strains with the disrupted transketolase gene was also somewhat retarded on a synthetic medium lacking aromatic amino acids phenylalanine and tyrosine although the effect was smaller than the effect of this mutation on D-xylulose utilization.

Transketolase genes from other yeast species can conveniently be cloned by complementation of the transketolase mutation in the S. cerevisiae strains described above. Preferably, the cloning can be performed by constructing a gene library of the non-Saccharomyces yeast strain in an appropriate vector (for example, the well known plasmid YEp13), transforming this library into a S. cerevisiae strain bearing transketolase mutation (for example, the mutants obtained by gene disruption described above) and selecting for transformants with restored growth on D-xylulose. The plasmid DNA can be rescued from such D-xylulose-positive transformants and used to transform the same recipient strain. All the clones from this transformation should be able to grow well on D-xylulose. Transketolase activity can be measured in the transformants and its reappearance at a significant level can serve as proof of the identity of the cloned gene. Additional and final proof can be obtained by sequencing short stretches of cloned DNA and finding pieces of sequence homologous to the *S. cerevisiae* transketolase gene sequence or by demonstrating hybridization of the cloned DNA fragment with the authentic transketolase clone from *S. cerevisiae*. Alternatively, the cloning procedure can be based on the DNA hybridization as primary method for selecting the clones containing the transketolase gene from the gene library of a non-Saccharomyces yeast. A fragment of the *S. cerevisiae* transketolase gene can be used as the probe for a colony or plaque hybridization experiment and the clones which give the strongest hybridization signal can be further analyzed by partial sequencing.

Whatever method is used for the cloning of transketolase gene from a chosen yeast species the subsequent steps for obtaining a mutation in the transketolase gene in this yeast are the same. The cloned DNA fragment should be characterized by constructing a partial restriction map and preferably localizing the coding region of the transketolase gene. Then a piece of DNA which can function as a selectable marker in the chosen yeast is inserted into the DNA fragment containing the transketolase gene not closer than several hundred bp from either of the termini of this fragment. The cassette containing the bacterial phleomycin gene under control of a strong yeast promoter, such as the above-described cassette from the plasmid pUT332, could for example, be used for many yeast species as a dominant selective marker. It is essential that the insertion of the DNA fragment bearing the selectable marker is done in such a fashion that the coding region of the transketolase gene is either disrupted by the inserted DNA or, preferably, the inserted DNA fragment substitutes (part of) the coding region. Such a DNA construct can then be used to disrupt the chromosomal copy of the transketolase gene in the selected yeast by a method similar to the method described above for obtaining the transketolase mutation in *S. cerevisiae*. Any suitable transformation method can be employed, the preferred methods are protoplast transformation and electroporation. The selection of the clones bearing the disrupted transketolase gene can be done similarly to the method described above for *S. cerevisiae*. Also, the analysis of the structure of the transketolase chromosomal region by Southern hybridization can be used as an alternative method or in addition to other methods.

Example 10

Cloning of the D-ribulokinase gene

The preferred way to clone the D-ribulokinase gene is similar to the method described in Example 1 for the cloning of the D-arabitol dehydrogenase. It is known that D-ribulokinase gene in several bacteria such as *E. coli* or *Klebsiella aerogenes* is a part of the ribitol utilization operon (Loviny, T. et al., *Biochem. J.* 230: 579–585 (1985)). It is also known that *E. coli* B strains do not contain this operon and are therefore incapable of utilizing ribitol as a carbon source. Thus, an *E. coli* B strain (such as common laboratory strains HB101 and JM103 or strains which can be transformed with high efficiency such as SCSI or XL1-Blue from Stratagene) can be transformed with a gene library of a ribitol-utilizing bacteria constructed in any suitable vector, preferably pUC19. Non-pathogenic bacterial species such as *Klebsiella terrigena* are the preferred source organisms for isolation of the D-ribulokinase gene. The *E. coli* transformants which are capable of growth on minimal medium containing ribitol as the sole carbon source can then be selected. The plasmid DNA from such ribitol-positive clones can be isolated and used to retransform an *E. coli* B strain. All transformants from such retransformation should be able to grow on ribitol as the sole carbon source. A restriction map of the cloned insert can then be constructed. Using this map various deletion derivatives of the original clone can be prepared and analyzed for the retention of ribitol operon by above-mentioned functional test. Several successive deletions can be performed in order to minimize the size of the DNA fragment bearing the ribitol operon to 3.5–4 kb (the size of this operon in *K. aerogenes*). Finally, (partial) nucleotide sequence of the D-ribulokinase gene can be determined and used to excise the coding region of this gene either using suitable naturally occurring restriction sites or using known PCR techniques for introduction of such sites. The D-ribulokinase gene can be expressed in other hosts, preferably yeasts, by a method that includes standard steps such as fusing the coding region of the D-ribulokinase gene to a suitable promoter and transcription terminator, transferring the expression cassette to a vector suitable for the transformation of the chosen host, obtaining the transformants and, finally verifying the efficiency of D-ribulokinase expression.

Example 11

Cloning and overexpression of the D-ribulose-5-phosphate-3-epimerase gene

The method for isolating homogeneous D-ribulose-5-phosphate-3-epimerase from baker's yeast (industrial *Saccharomyces cerevisiae* yeast) is known (Williamson, W. T. et al., *Meth. Enzymol.* 9: 605–608 (1966)). The enzyme can be isolated and the N-terminal as well as partial internal amino acid sequences determined by the generally known methods. Thus obtained partial amino acid sequences can then be used to generate, by a procedure known as reverse translation, the sequences of oligonucleotides which then can be used to prime the polymerase chain reaction. The DNA fragments generated by PCR can be used as hybridization probes to screen a yeast gene library for a full length copy of the D-ribulose-5-phosphate-3-epimerase gene. The preferred way to overexpress the D-ribulose-5-phosphate-3-epimerase gene in other yeast hosts is to clone it into a vector which has a high copy number in the desired host (for example, pSRT303D vector for *Z. rouxii*). An alternative and more efficient way of overexpressing the gene is to determine at least a partial nucleotide sequence of the D-ribulose-5-phosphate-3-epimerase gene around the translation start codon and use this information for isolating the coding sequence of the D-ribulose-5-phosphate-3-epimerase gene and fusing it to a promoter known to function efficiently in the chosen host.

Example 12

Cloning of the D-xylulokinase gene and construction of D-xylulokinase routants

Methods for cloning of the D-xylulokinase (EC 2.7.1.17) gene from different yeast species have been described (Ho, N. W. Y. et at., *Enzyme Microbiol. Technol.* 11: 417–421 (1989); Stevis, P. E. et al., *Applied and Environmental Microbiol.* 53: 2975–2977 (1987)). Also, a method for constructing the D-xylulokinase mutation in *S. cerevisiae* by gene disruption has been described (Stevis, P. E. et al., *Appl.*

*Biochem. Biotechnol.* 20: 327–334 (1989)). Similar methods can be used for constructing D-xylulokinase routants in other yeasts. For the yeast species other than *S. cerevisiae*, the genetic markers used for the disruption of D-xylulokinase gene are preferably dominant antibiotic resistance markers (see Example 9). Alternatively, classical mutant construction methods based on chemical (for example, treatment with ethyl methane sulfonate or acriflavine) or physical (ultraviolet light, X-rays) mutagenesis can be employed. The mutant enrichment can be performed by growing the mutagenized cells on D-xylulose as the sole carbon source in the presence of antibiotic (such as nystatin) which kills only growing cells. The inability of D-xylulokinase routants to utilize D-xylulose as the sole carbon source for growth can be used for the selection of mutants.

Example 13

Strains producing xylitol via D-arabitol with improved yield

Example 4 describes the method for the construction of a yeast strain capable of producing xylitol from structurally unrelated carbon sources such as D-glucose by a pathway which utilizes D-arabitol as the key intermediate. To improve xylitol yield in fermentations with the strains utilizing this "D-arabitol pathway"—the D-arabitol yield must be improved. The pathway leading from D-glucose to D-arabitol in D-arabitol-producing yeasts has been described (Ingram, J. M. et al., *J. Bacteriol.* 89: 1186–1194 (1965)). D-arabitol is produced from D-ribulose-5-phosphate via dephosphorylation and reduction with a NADPH-linked D-ribulose reductase. Formation of D-ribulose-5-phosphate from D-glucose 6-phosphate by two successive irreversible dehydrogenation steps with D-glucose-6-phosphate dehydrogenase and 6-phospho-D-gluconate dehydrogenase is a universally occurring pathway known as the oxidative branch of the pentose phosphate pathway (or hexose monophosphate shunt). In the non-oxidative branch of the pentose phosphate pathway, D-ribulose-5-phosphate is reversibly isomerized into ribose-5-phosphate and D-xylulose-5-phosphate. Ribose-5-phosphate and D-xylulose-5-phosphate are further metabolized by transketolase. Therefore, transketolase can be mutated in an D-arabitol-producing microbial strain and the fraction of D-ribulose-5-phosphate converted into D-arabitol will be increased. Example 9 describes the method for obtaining the transketolase mutants. Further increase of the D-arabitol yield can be achieved if the rate of D-ribulose-5-phosphate biosynthesis is maximized through overexpression of the two genes coding for the enzymes of the oxidative branch of the pentose phosphate pathway as described above (Example 9). The strains optimized by this method with respect to the D-arabitol yield can then be further transformed with recombinant DNA constructions bearing the xylitol dehydrogenase and D-arabitol dehydrogenase genes (Examples 3 and 4) resulting in strains with improved efficiency of xylitol production.

Example 14

Strains producing xylitol by alternative pathways

The method according to Examples 4 and 13 are the most straightforward methods for the construction of microbial strains capable of converting D-glucose and other carbon sources into xylitol. These methods utilize the naturally occurring pathway leading to the formation of D-arabitol from various carbon sources and extend this pathway by two more reactions to convert D-arabitol into xylitol. However, this pathway is not the only possible pathway. Other pathways leading to xylitol as a final metabolic product and not involving D-arabitol as an intermediate can be constructed. Thus, a pathway to xylitol from the same precursor - D-ribulose-5-phosphate can be realized through a different chain of reactions. D-ribulose-5-phosphate can efficiently be converted to D-xylulose-5-phosphate by D-ribulose-5-phosphate-3-epimerase (Example 11) and if further conversion of D-xylulose-5-phosphate is prevented by a mutation in the transketolase gene, the accumulated D-xylulose-5-phosphate can be dephosphorylated by the same non-specific phosphatase as D-ribulose-5-phosphate (Ingram, J. M. et al., *J. Bacteriol.* 89: 1186–1194 (1965)) and reduced into xylitol by xylitol dehydrogenase (Example 3). Realization of this pathway can further require the inactivation of D-xylulokinase gene (Example 12) in order to minimize the energy loss due to the futile loop: D-xylulose-5-phosphate→D-xylulose→D-xylulose-5-phosphate. An additional genetic change—introduction and (over)-expression of the D-ribulokinase gene (E.C. 2.7.1.47) could minimize simultaneous D-arabitol production by such strains by trapping the D-ribulose produced by the unspecific phosphatase. The D-ribulose will be converted back into the D-ribulose-5-phosphate and further into D-xylulose-5-phosphate.

Example 15

Stability of the recombinant *Z. rouxii* strain and production of xylitol under conditions of fermentor cultivation The stability of xylitol production during extended cultivation was checked in both selective conditions (using the selective medium: YEPD containing 50 mg/liters G418 and 30% glucose) and non-selective conditions (using the same medium without G418). A single freshly obtained transformant of *Z. rouxii* ATCC 13356 [pSRT(AX)-9)] was grown in a 200 ml volume of G418 containing YEPD. The cells were transferred into 50% glycerol solution and frozen at −70° C. in 1 ml aliquotes. Four frozen aliquotes of *Z. rouxii* [pSRT(AX)-9)] were used to inoculate two 50-ml cultures in selective medium and two in non-selective medium. After the cultures reached the stationary phase of growth (50–60 h at 30° C. and 200 rpm) a sample was taken for the HPLC analysis of pentitol content and 1 ml of the culture was used to inoculate another 50 ml of the same (either selective or non-selective) medium. The growth-dilution cycle was repeated four more times. The conditions of this experiment approximate the propagation of the recombinant strain from a standard frozen inoculum in a large scale fermentation. The results of this experiment are presented in Table 7. Predictably, the stability of the recombinant strain is higher on the selective medium. However, even under non-selective medium the decline in xylitol yield was only detected after approximtely 20 generations. Under selective conditions, the xylitol production was stable for approximately 30 generations.

An aliquote of the frozen stock of the transformed *Z. rouxii* strain was used to inoculate a 2 liter fermentor containing 1 liter of medium having the following composition (per liter): 0.1 g NaCl, 6.8 g potassium phosphate, 0.5 g ammonium sulphate, 20 g of yeast extract and 400 g of glucose, 50 mg of G481, pH 6.0. The cultivation conditions were: aeration rate, 0.5 v/min; agitation, 400 rpm; temperature, 30° C.

FIG. 10 shows the time course of the glucose consumption and xylitol accumulation in this fermentation. The concentration of dissolved oxygen which reflects the respiritory activity of the yeast culture is also shwon. An apparent biphasic growth was observed: in the first phase, a plateau in glucose and xylitol concentration was reached in about forty hours (less than half of the available glucose was consumed at that point), the second phase was observed after approximately 200 hours of cultivation when the glucose consumption and xylitol production resumed. The final xylitol concentration was 15 g/liter, almost two times higher than the concentration obtained in the flask fermentations. The biphasic growth with a long lag period indicated that a spontaneous mutant was selected (presumably having a higher alcohol tolerance than the parent strain). To check this hypothesis, a single clone was isolated from the culture at the endpoint of the fermentor run. This isolate was grown in a fermentor under the conditions identical to those described above. The results of this experiment (FIG. 11) confirmed that a mutant capable of complete assimilation of 400 g/liter glucose in about 60 hours was indeed isolated. This experiment also shows that the xylitol-producing *Z. rouxii* strain can also assimilate xylitol when all the glucose in the culture medium is consumed.

TABLE 7

Stability of xylitol production by the strain
*Z. rouxii* ATCC 13356 [pSRT(AX)-9] under conditions of serial
cultivation (g/liter, normalized by total pentitol yield).

| | | Cultivation conditions | |
|---|---|---|---|
| Serial Dilution No. | Culture No. | Selective | Non-Selective |
| 1 | 1 | 8.3 | 8.6 |
|   | 2 | 8.9 | 8.6 |
| 2 | 1 | 8.9 | 8.9 |
|   | 2 | 8.5 | 8.4 |
| 3 | 1 | 8.5 | 8.3 |
|   | 2 | 8.6 | 8.2 |
| 4 | 1 | 8.7 | 8.0 |
|   | 2 | 8.6 | 6.9 |
| 5 | 1 | 8.6 | 7.6 |
|   | 2 | 8.1 | 5.6 |
| 6 | 1 | 7.0 | 7.0 |
|   | 2 | 6.9 | 2.4 |

All references are incorporated herein by reference. Having now fully described the invention, it will be understood by those with skill in the art that the scope can be performed with a wide and equivalent range of concentrations, parameters, and the like, without affecting the spirit or scope of the invention or any embodiment thereof.

What is claimed is:

1. A method for production of xylitol from a recombinant microbial host, wherein said method comprises:
   a) growing an arabitol-producing yeast or an arabitol-producing fungus under conditions that provide for synthesis of said xylitol, wherein said arabitol-producing yeast or said arabitol-producing fungus has been modified to synthesize xylitol as an end product in a single fermentation when grown on D-arabitol or a carbon source that the unmodified arabitol-producing yeast or unmodified arabitol-producing fungus utilized for D-arabitol biosynthesis, said carbon source being other than D-xylose, D-xylulose, mixtures of D-xylose and D-xylulose, and polymers and oligomers containing D-xylose or D-xylulose as major components under conditions that provide for synthesis of said xylitol wherein before said modification said host produced D-arabitol but did not utilize said D-arabitol for the synthesis of xylitol, and wherein said host has been transformed with a DNA encoding a D-xylulose forming D-arabitol dehydrogenase (E.C. 1.1.1.11) and with a DNA encoding xylitol dehydrogenase (E.C. 1.1.1.9); and b) recovering said xylitol produced in step a.

2. The method of claim 1, wherein said host does not express D-xylulokinase (EC 2.7.1.17).

3. The method of claim 1, wherein said host does not express transketolase (EC 2.2.1.1).

4. The method of claim 1, wherein said host is transformed with one or more coding sequences selected from the group consisting of DNA encoding D-glucose-6-phosphate dehydrogenase (EC 1.1.1.49), 6-phospho-D-gluconate dehydrogenase (EC 1.1.1.44), and D-ribulose-5-phosphate-3-epimerase (EC 5.1.3.1).

5. The method of any one of claims 1, 2–4, wherein said yeast is selected from the group consisting of *Z. rouxii* and *Candida polymorpha, Torulopsis candida, Pichia farinosa, Torulaspora hansenii*, and said fungus is selected from the group consisting of *Dendryphiella salina* and *Schizophyllum commune*.

6. The method of claim 5, wherein said yeast is *Z. rouxii*.

7. The method of claim 4, wherein said group consists of DNA encoding D-glucose-6-phosphate dehydrogenase (EC 1.1.1.49), and 6-phospho-D-gluconate dehydrogenase (EC 1.1.1.44).

8. The method of claim 1, wherein said host forms xylitol by converting D-xylulose-5-phosphate to D-xylulose followed by reduction of D-xylulose to xylitol.

9. The method of claim 8 wherein said host is further transformed with a DNA construct encoding one or more enzymes selected from the group consisting of D-glucose-6-phosphate dehydrogenase (EC 1.1.1.49), 6-phospho-D-gluconate dehydrogenase (EC 1.1.1.44), D-ribulose-5-phosphate-3-epimerase (EC 5.1.3.1), D-ribulokinase (EC 2.7.1.47).

10. The method of claim 9, wherein said group consists of D-glucose-6-phosphate dehydrogenase (EC 1.1.1.49), 6-phospho-D-gluconate dehydrogenase (EC 1.1.1.44).

11. The method of claim 8, wherein said host does not express transketolase (EC 2.2.1.1).

12. The method of claim 11 wherein said host is further transformed with a DNA construct encoding one or more enzymes selected from the group consisting of D-glucose-6-phosphate dehydrogenase (EC 1.1.1.49), 6-phospho-D-gluconate dehydrogenase (EC 1.1.1.44), D-ribulose-5-phosphate-3-epimerase (EC 5.1.3.1), D-ribulokinase (EC 2.7.1.47).

13. The method of claim 12, wherein said group consists of D-glucose-6-phosphate dehydrogenase (EC 1.1.1.49), 6-phospho-D-gluconate dehydrogenase (EC 1.1.1.44).

14. The method of claim 8, wherein said host does not express D-xylulokinase (EC 2.7.1.17).

15. The method of claim 14 wherein said host is further transformed with a DNA construct encoding one or more enzymes selected from the group consisting of D-glucose-6-phosphate dehydrogenase (EC 1.1.1.49), 6-phospho-D-gluconate dehydrogenase (EC 1.1.1.44), D-ribulose-5-phosphate-3-epimerase (EC 5.1.3.1), D-ribulokinase (EC 2.7.1.47).

16. The method of claim 15 wherein said group consists of D-glucose-6-phosphate dehydrogenase (EC 1.1.1.49), 6-phospho-D-gluconate dehydrogenase (EC 1.1.1.44).

17. The method of claim 8, wherein said host does not express transketolase (EC 2.2.1.1) and D-xylulokinase (EC 2.7.1.17).

18. The method of claim 17 wherein said host is further transformed with a DNA construct encoding one or more enzymes selected from the group consisting of D-glucose-6-phosphate dehydrogenase (EC 1.1.1.49), 6-phospho-D-gluconate dehydrogenase (EC 1.1.1.44), D-ribulose-5-phosphate-3-epimerase (EC 5.1.3.1), D-ribulokinase (EC 2.7.1.47).

19. The method of claim 18, wherein said group consists of D-glucose-6-phosphate dehydrogenase (EC 1.1.1.49), 6-phospho-D-gluconate dehydrogenase (EC 1.1.1.44).

20. The method of any one of claims 8, 9, 11, 12, 14, 15, 17 or 18, wherein said yeast is selected from the group consisting of *Zygosaccharomyces rouxii, Candida polymorpha, Torulopsis candida, Pichia farinosa, Torulaspora hansenii*, and said fungus is selected from the group consisting of *Dendryphiella salina* and *Schizophyllum commune*.

21. The method of claim 20, wherein said yeast is *Z. rouxii*.

22. A recombinant host, wherein said host is a modified arabitol-producing yeast or a modified arabitol-producing fungus and wherein as a result of said modification said host synthesizes xylitol in a single fermentation when grown on D-arabitol or a carbon source that the unmodified host utilizes for D-arabitol biosynthesis, said carbon source being other than D-xylose, D-xylulose, mixtures of D-xylose and D-xylulose, or polymers or oligomers containing D-xylose and/or D-xylulose as major component, said synthesis being greater than that of the corresponding non-recombinant microbial host, wherein said recombinant host has been transformed with a DNA encoding D-arabitol dehydrogenase (E.C. 1.1.1.11) and with a DNA encoding xylitol dehydrogenase (E.C. 1.1.1.9).

23. The recombinant host of claim 22, wherein said host does not express D-xylulokinase (EC 2.7.1.17).

24. The recombinant host of claim 22, wherein said host does not express transketolase (EC 2.2.1.1).

25. The recombinant host of claim 22, wherein said host does not express D-xylulokinase (EC 2.7.1.17) or transketolase (EC 2.2.1.1).

26. The recombinant host of claim 22, wherein said host is transformed with a gene encoding D-glucose-6-phosphate dehydrogenase (EC 1.1.1.49).

27. The recombinant host of claim 22, wherein said host is transformed with a gene encoding 6-phospho-D-gluconate dehydrogenase (EC 1.1.1.44).

28. The recombinant host of claim 22, wherein said yeast is selected from the group consisting of *Zygosaccharomyces rouxii, Candida polymorpha, Torulopsis candida, Pichia farinosa, Torulaspora hansenii*, and said fungus is selected from *Dendryphiella salina* and *Schizophyllum commune*.

29. The recombinant host of claim 28, wherein said yeast is *Z. rouxii*.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: both ( x i ) SEQUENCE DESCRIPTION: SEQ ID NO:1:

CGAATTCTAG ACCACCCTAA GTCGTCCC        28

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: both ( x i ) SEQUENCE DESCRIPTION: SEQ ID NO:2:

TTCAAGAATT CAAGAAACTC ACGTGATGC        29

( 2 ) INFORMATION FOR SEQ ID NO:3:

( i ) SEQUENCE CHARACTERISTICS:
        ( A ) LENGTH: 26 base pairs (B) TYPE: nucleic acid
(C) STRANDEDNESS: both
(D) TOPOLOGY: both ( x i ) SEQUENCE DESCRIPTION: SEQ ID NO:3:

CAGGCCGTCG ACAAGGATCT CGTCTC                                                              26

( 2 ) INFORMATION FOR SEQ ID NO:4:

( i ) SEQUENCE CHARACTERISTICS:
(A) LENGTH: 33 base pairs
(B) TYPE: nucleic acid
(C) STRANDEDNESS: both
(D) TOPOLOGY: both ( x i ) SEQUENCE DESCRIPTION: SEQ ID NO:4:

AATTAGTCGA CCGTTAATTG GGGCCACTGA GGC                                                      33

( 2 ) INFORMATION FOR SEQ ID NO:5:

( i ) SEQUENCE CHARACTERISTICS:
(A) LENGTH: 35 base pairs
(B) TYPE: nucleic acid
(C) STRANDEDNESS: both
(D) TOPOLOGY: both ( x i ) SEQUENCE DESCRIPTION: SEQ ID NO:5:

GCGAAGCTTA AAAATGTCCA AGCAACAGAT CGGCG                                                    35

( 2 ) INFORMATION FOR SEQ ID NO:6:

( i ) SEQUENCE CHARACTERISTICS:
(A) LENGTH: 34 base pairs
(B) TYPE: nucleic acid
(C) STRANDEDNESS: both
(D) TOPOLOGY: both ( x i ) SEQUENCE DESCRIPTION: SEQ ID NO:6:

GCGAAGCTTA GATTAATCCA GCCATTCGGT ATGG                                                     34

( 2 ) INFORMATION FOR SEQ ID NO:7:

( i ) SEQUENCE CHARACTERISTICS:
(A) LENGTH: 44 base pairs
(B) TYPE: nucleic acid
(C) STRANDEDNESS: both
(D) TOPOLOGY: both ( x i ) SEQUENCE DESCRIPTION: SEQ ID NO:7:

AGCTCTAGAA ATGACTCAAT TCACTGACAT TGATAAGCTA GCCG                                          44

( 2 ) INFORMATION FOR SEQ ID NO:8:

( i ) SEQUENCE CHARACTERISTICS:
(A) LENGTH: 44 base pairs
(B) TYPE: nucleic acid
(C) STRANDEDNESS: both
(D) TOPOLOGY: both ( x i ) SEQUENCE DESCRIPTION: SEQ ID NO:8:

GGAGAATTCA GCTTGTCACC CTTATAGAAT GCAATGGTCT TTTG                                          44